United States Patent
Bavington et al.

(10) Patent No.: US 9,453,082 B2
(45) Date of Patent: Sep. 27, 2016

(54) POLYSACCHARIDES FROM PRASINOCOCCALES

(71) Applicant: Glycomar Limited, Dunbeg, Oban, Argyll (GB)

(72) Inventors: Charles Daniel Bavington, Highland (GB); Claire Moss, Highland (GB)

(73) Assignee: GLYCOMAR LIMITED (GB)

( * ) Notice: Subject to any disclaimer, the term of this patent is extended or adjusted under 35 U.S.C. 154(b) by 0 days.

(21) Appl. No.: 14/398,528

(22) PCT Filed: May 13, 2013

(86) PCT No.: PCT/GB2013/051223
§ 371 (c)(1),
(2) Date: Nov. 3, 2014

(87) PCT Pub. No.: WO2013/167911
PCT Pub. Date: Nov. 14, 2013

(65) Prior Publication Data
US 2015/0119355 A1   Apr. 30, 2015

(30) Foreign Application Priority Data

May 11, 2012 (GB) .................................. 1208325.9

(51) Int. Cl.
| | | |
|---|---|---|
| C08B 37/00 | (2006.01) | |
| A61K 31/737 | (2006.01) | |
| A61K 36/05 | (2006.01) | |
| A61K 8/73 | (2006.01) | |
| C12P 19/04 | (2006.01) | |

(52) U.S. Cl.
CPC .............. *C08B 37/006* (2013.01); *A61K 8/73* (2013.01); *A61K 31/737* (2013.01); *A61K 36/05* (2013.01); *C12P 19/04* (2013.01)

(58) Field of Classification Search
CPC .......................... C08B 37/006; A61K 31/737
See application file for complete search history.

(56) References Cited

FOREIGN PATENT DOCUMENTS

WO   2011031161 A1   3/2011

OTHER PUBLICATIONS

Kurano et al., Energy Convers. Mgmt., 1995, 36(6-9), p. 689-692.*
International Search Report and Written Opinion dated Aug. 21, 2013 for PCT/GB2013/051223.
MCN Si Eburth John et al: "Widespread occurrence of the oceanic ultraplankter Prasinococcus capsulatus (Prasinophyceae) the diagnostic "Golgi-decapore complex" and the newly described polysaccharide "capsulan"", Journal of Phycology, vol. 35, No. 5. Oct. 1999, pp. 1032-1043. XP002704952.
Miyashita, et al. *Prasinococcus capsulatus* Gen. Et Sp. Nov., A New Marine Coccoid Prasinophyte. J. Gen. Appl. Microbiol., 39, 571-582 (1993).
Guillard R. and Ryther J. 1962 Studies of marine planktonic diatoms. Can. J. Microbiol.8: 229-239.
Rota C. et al. 2005 Free radical generation during chemical depolymerization of heparin. Anal Biochem. 344(2):193-203.
Petit AC et al. 2006 Free-radical depolymerization with metallic catalysts of an exopolysaccharide produced by a bacterium isolated from a deep-sea hydrothermal vent polychaete annelid. Carbohydrate Polymers 64: 597-602.
Terho T & Hartiala K. Method for the determination of sulphate content of glycosaminoglycans. Analytical Biochemistry (1971) 41 (2): 471-476.
Higashi et al. Controlled photochemical depolymerization of K5 heparosan, a bioengineered heparin precursor, Carbohydrate Polymers 86 (2011) 1365-1370.
Miyashita, et al. Composition and nature of extracellular polysaccharide produced by newly isolated coccoid prasinophyte, Prasinococcus capsulatus. J. Marine Biotechnol., 3, 136-139 (1995).

* cited by examiner

*Primary Examiner* — Jonathan S Lau
(74) *Attorney, Agent, or Firm* — Abel Law Group, LLP

(57) ABSTRACT

There is provided a composition comprising a polysaccharide obtainable from the microalgae, *Prasinococcus capsulatus* and strains related to *P. capsulatus* for use prophylactically and/or therapeutically in the treatment of disorders of the immune system, for example in psoriasis and dermatological conditions, internal immune system disorders, in particular gut inflammatory conditions and respiratory conditions. Further, there is provided derivatives of a polysaccharide obtainable from the microalgae, *Prasinococcus capsulatus* or an algal strain related to *P. capsulatus* and the use of such derivatives prophylactically and/or therapeutically in the treatment of disorders of the immune system.

15 Claims, 26 Drawing Sheets

| RT | Area | % Area | Retention time | Start time | End time | Calc. MW / kDa |
|---|---|---|---|---|---|---|
| 6.0 | 15667 | 100 | 6.0 | 5.333 | 10.65 | >670 |

Example batch 1:

Example batch 2:

| Standards | Retention Time | Area | Ratio |
|---|---|---|---|
| Arabinose | 6.848 | 177742.5 | 0.34 |
| Rhamnose | 7.368 | 336084.4 | 0.64 |
| Fucose | 7.847 | 136171.1 | 0.26 |
| Xylose | 8.803 | 225926.8 | 0.43 |
| GalA | 10.644 | 105925.6 | 0.20 |
| Mannose | 11.129 | 262125.1 | 0.50 |
| Galactose | 11.936 | 154690.4 | 0.29 |
| Glucose | 13.065 | 202270.3 | 0.39 |
| GlcA | 13.778 | 132357.6 | 0.25 |
| Scyllo Inositol | 15.821 | 524677.6 | n/a |
| GlcNAc | 16.525 | 30715.8 | 0.06 |
| GalNAc | 17.029 | 59821.6 | 0.11 |

| Standards | Ratio | Std ratio | nMoles | % |
|---|---|---|---|---|
| Arabinose | 0.37 | 0.29 | 6.38 | 14.17 |
| Rhamnose | 0.12 | 0.54 | 1.1 | 2.45 |
| Fucose | | 0.25 | 0 | 0 |
| Xylose | 0.06 | 0.36 | 0.85 | 1.89 |
| GalA | | 0.17 | 0 | 0 |
| Mannose | 0.14 | 0.46 | 1.48 | 3.3 |
| Galactose | 1.14 | 0.27 | 21.12 | 46.92 |
| Glucose | 0.99 | 0.38 | 12.88 | 28.61 |
| GlcA | 0.05 | 0.22 | 1.2 | 2.66 |
| GlcNAc | | 0.07 | 0 | 0 |
| GalNAc | | 0.1 | 0 | 0 |

| Standards | Ratio | Std ratio | nMoles | % |
|---|---|---|---|---|
| Arabinose | 0.56 | 0.34 | 8.26 | 8.47 |
| Rhamnose | 0.09 | 0.64 | 0.68 | 0.7 |
| Fucose | | 0.26 | 0 | 0 |
| Xylose | 0.18 | 0.43 | 2.04 | 2.09 |
| GalA | 0.09 | 0.2 | 2.22 | 2.29 |
| Mannose | | 0.5 | 0 | 0 |
| Galactose | 3.28 | 0.29 | 56.5 | 57.99 |
| Glucose | 1.87 | 0.39 | 23.97 | 24.6 |
| GlcA | 0.19 | 0.25 | 3.76 | 3.86 |
| GlcNAc | | 0.06 | 0 | 0 |
| GalNAc | | 0.11 | 0 | 0 |

| Standards | Ratio | Std ratio | nMoles | % |
|---|---|---|---|---|
| Arabinose | 0.45 | 0.34 | 6.67 | 5.68 |
| Rhamnose | 0.29 | 0.64 | 2.26 | 1.92 |
| Fucose |  | 0.26 | 0 | 0 |
| Xylose |  | 0.43 | 0 | 0 |
| GalA | 0.18 | 0.2 | 4.58 | 3.89 |
| Mannose | 0.38 | 0.5 | 3.76 | 3.2 |
| Galactose | 2.48 | 0.29 | 42.75 | 36.34 |
| Glucose | 3.45 | 0.39 | 44.22 | 37.59 |
| GlcA | 0.67 | 0.25 | 13.38 | 11.38 |
| GlcNAc |  | 0.06 | 0 | 0 |
| GalNAc |  | 0.11 | 0 | 0 |

Figure 3e

|  | Large polysaccharide fragment | | Small polysaccharide fragment | | Small polysaccharide fragment | |
| --- | --- | --- | --- | --- | --- | --- |
|  | HPAEC-PAD | GC-FID | HPAEC-PAD | GC-FID | HPAEC-PAD | GC-FID |
| Arabinose | 2.37 | 10.86 | 2.63 | 5.62 | 3.18 | 6.57 |
| Rhamnose | 0.43 | 1.44 | 0.83 | 1.36 | 0.84 | 1.41 |
| Fucose | 0.10 | 0.00 | 0.06 | 0.00 | 0.07 | 0.00 |
| Xylose | 0.51 | 1.76 | 1.20 | 1.74 | 1.11 | 1.41 |
| Galacturonic acid | 0.93 | 0.00 | 1.29 | 3.24 | 1.28 | 3.22 |
| Mannose | 0.00 | 0.00 | 0.37 | 0.92 | 0.35 | 1.03 |
| Galactose | 11.80 | 37.50 | 21.58 | 37.63 | 18.94 | 34.53 |
| Glucose | 82.24 | 45.31 | 68.27 | 42.52 | 71.02 | 45.07 |
| Glucuronic acid | 1.00 | 3.12 | 2.88 | 6.97 | 2.50 | 6.76 |

|  | HMW polysaccharide | | HMW polysaccharide | | HMW polysaccharide | |
| --- | --- | --- | --- | --- | --- | --- |
|  | HPAEC-PAD | GC-FID | HPAEC-PAD | GC-FID | HPAEC-PAD | GC-FID |
| Arabinose | 3.61 | 13.79 | 2.31 | 5.25 | 3.51 | 6.80 |
| Rhamnose | 0.60 | 2.47 | 0.40 | 0.86 | 0.69 | 1.07 |
| Fucose | 0.03 | 0.00 | 0.03 | 0.00 | 0.07 | 0.00 |
| Xylose | 0.95 | 1.64 | 1.26 | 1.72 | 0.81 | 1.76 |
| Galacturonic acid | 0.70 | 0.00 | 0.68 | 1.92 | 0.78 | 0.00 |
| Mannose | 0.59 | 2.37 | 0.34 | 0.97 | 0.43 | 0.93 |
| Galactose | 33.70 | 47.26 | 34.22 | 64.63 | 33.26 | 58.75 |
| Glucose | 57.68 | 29.62 | 58.75 | 21.71 | 57.75 | 26.68 |
| Glucuronic acid | 1.77 | 2.86 | 1.66 | 2.93 | 2.39 | 4.01 |

Chi squared = 0.2930

Parameters:
ci      = 0.8165
sigma   = 11.9615
ri      = 7.1200
E       = -1.1688e-2

Standard deviations:
Δci     = 1.0079e-2
Δsigma  = 0.2458
ΔE      = 4.3565e-3

M = 38.62 MDa

Figure 16a

|  | Average values for native HMW polysaccharide: | Average values for LMW depolymerised fragments of polysaccharide: | Average values for large depolymerised fragments: |
|---|---|---|---|
| Molecular weight / kDa | >670, with some smaller material <20 | 2-10 | 20-60 |
| Sulphate content / % | 19 | 26 | 25 |
| Monosaccharide composition % | Glucose 25-28 Galactose 35-45 Arabinose 15 Uronics 4-6 Others: xylose / rhamnose | Glucose 35 Galactose 35 Arabinose 11 Uronics 9 Others: xylose/ rhamnose | Glucose 25-28 Galactose 35-45 Arabinose 15 Uronics 4-6 Others: xylose / rhamnose |
| Cytotoxicity (0.1mg/ml) / % | 93 | 107 | 89 |
| Neutrophil elastase activity (0.1mg/ml) / % | 38 | 15 | 25 |
| Oxidative burst (0.1mg/ml) / % | 73 | 64 | 69 |
| IL8 release from keratinocytes (0.1mg/ml) / % | NA | 23 | 23 |
| IL8 gene expression (0.1mg/ml) / % | NA | 21 | 23 |

Figure 16b

| Sample | % sulphate by Terho method | % sulphate by ICP-OES |
|---|---|---|
| HMW polysaccharide 06111201 | 20 | 31 |
| HMW polysaccharide 19111203 | 30.4 | 31 |
| HMW polysaccharide 11121201 | 26.8 | 31 |
| HMW polysaccharide 14011302 | 28.2 | 30 |
| LMW polysaccharide 01021302 | 35 | 33 |

POLYSACCHARIDES FROM PRASINOCOCCALES

FIELD OF THE INVENTION

The invention relates to a composition comprising a polysaccharide obtainable from the microalgae, *Prasinococcus capsulatus* and strains related to *P. capsulatus* for use prophylactically and/or therapeutically in the treatment of disorders of the immune system, such as inflammatory disorders, for example in psoriasis and dermatological conditions. Further, there is provided derivatives of a polysaccharide obtainable from the microalgae, *Prasinococcus capsulatus* or an algal strain related to *P. capsulatus* and the use of such derivatives prophylactically and/or therapeutically in the treatment of disorders of the immune system, such as inflammatory disorders, for example in psoriasis and dermatological conditions.

Also provided is the use of polysaccharide and derivatives thereof obtainable from the microalgae, *Prasinococcus capsulatus* or an algal strain related to *P. capsulatus* in the preparation of cosmetic and nutritional compositions.

BACKGROUND OF THE INVENTION

Macroalgae (seaweeds) have been exploited to provide long established products such as alginate and carageenan and newer products such as fucoidan; however, microalgae have not yet been significantly used in this way and there has been relatively little characterisation of those products derived from microalgae.

SUMMARY OF THE INVENTION

According to a first aspect of the invention there is provided a gel forming polysaccharide obtainable from *Prasinococcus capsulatus* or an algal strain related to *P. capsulatus* wherein the gel forming polysaccharide is a sulphated heteropolymer of molecular weight greater than 670 kDa comprising glucose, galactose, arabinose and uronic acid units for use in the treatment of immune system disorders, in particular immune system disorders which are inflammatory conditions.

The inventors have undertaken a range of methods to determine the composition of the polysaccharide of the invention and the derivatives thereof. Using the methods detailed herein, without wishing to be bound by theory as to the configuration of the polysaccharide, the inventors have characterised the polysaccharide and derivatives as described. Therefore, in embodiments when a polysaccharide or derivatives are characterised using the methods described herein they provide the monosaccharide and sulphate compositions as described herein.

*Prasinococcus capsulatus*, a relatively recently discovered species has been shown to produce polysaccharides (Miyashita, et al. *Prasinococcus capsulatus* Gen. Et Sp. Nov., A New Marine Coccoid Prasinophyte. J. Gen. Appl. Microbiol., 39, 571-582 (1993) and Miyashita, et al. Composition and nature of extracellular polysaccharide produced by newly isolated coccoid prasinophyte, *Prasinococcus capsulatus*. J. Marine Biotechnol., 3, 136-139 (1995).).

Suitably a strain related to *Prasinococcus capsulatus* may include a strain of the order Prasinococcales. In embodiments a strain related to *Prasinococcus capsulatus* can include *Prasinoderma singularis*. In embodiments the polysaccharide can be polysaccharide associated with the cell wall of the microalgae, and/or be present in a homengenate of the microalgae, and/or secreted polysaccharide or exopolysaccharide. The polysaccharide may be provided in an isolated, purified, or semi-purified form. In embodiments the polysaccharides can be a purified material that has been separated from cell biomass, such that the polysaccharide is at least 50% polysaccharide by weight, and more preferably above 75% polysaccharide by weight, more preferably above 85% by weight, more preferably about 95% by weight.

In embodiments, immune system disorders are those where the response of vascular cells and tissues to internal or external stimuli is insufficient, excessive or chronic. In inflammatory conditions this response is generally excessive and/or chronic resulting in increased and maintained activation of immune cells (such as neutrophils and T-cells), which may infiltrate tissues and increase production of pro-inflammatory mediators, resulting in sustained inflammation. It has been determined that polysaccharides can be used to moderate the effects of this activation, for example, by reducing the activity of neutrophil proteases, such as elastase; by reducing the secretion of pro-inflammatory proteins (cytokines) and reactive oxygen species from blood and endothelial cells; and by reducing blood cell infiltration to effected tissues.

In embodiments of the invention, a polysaccharide as described herein can be for use in the treatment of inflammatory skin conditions, including eczema, psoriasis and atopic dermatitis.

In embodiments of the invention a polysaccharide as described herein can be for use in the treatment of inflammatory conditions of the gut, in particular for use in the treatment of bowel disorders, including irritable bowel syndrome, Crohn's disease and ulcerative colitis.

In embodiments of the invention a polysaccharide as described herein can be for use in the treatment of respiratory inflammatory conditions including asthma, cystic fibrosis, emphysema, chronic obstructive pulmonary disorder, acute respiratory distress syndrome, or allergic rhinitis.

Embodiments of the polysaccharide for use in the invention can be characterised by at least one, at least two, at least three, at least four, or at least five of the characteristics (i), (ii), (iii), (iv), and (v).
(i) Molecular weight range
(ii) Monosaccharide composition
(iii) Immunomodulatory activity
(iv) Sulphate content (as a percentage of molecular weight of the molecule)
(v) Viscosity/gel-forming properties Molecular Weight Range A polysaccharide for use in the present invention typically has a molecular weight of 670 kDa or greater than 670 kDa.

In embodiments the polysaccharide of the invention can have a molecular weight in the range of 670 kDa to 40 MegaDa. In embodiments, the polysaccharide of the invention can have a molecular weight greater than or equal to 1 MegaDa, greater than or equal to 5MegaDa, greater than or equal to 10 MegaDa, greater than or equal to 15 MegaDa, greater than or equal to 20 MegaDa, greater than or equal to 25 MegaDa, greater than or equal to 30 MegaDa, greater than or equal to 35 MegaDa, or 40 MegaDa.

In embodiments a polysaccharide of the present invention can comprise about
20 to 30% Glucose
30 to 60% Galactose
4 to 19% Arabinose
2 to 6% Uronic acids and a small percentage (1 to 10%) of other sugars, more particularly
1-4% Rhamnose
1-3% Xylose
1-10% Mannose
(% by weight).

In embodiments a polysaccharide of the present invention can comprise about
25 to 29% Glucose
35 to 47% Galactose
14 to 15% Arabinose
4 to 6% Uronic acids
and a small percentage (1 to 4%) of other sugars, more particularly
2.4% Rhamnose
1.8% Xylose
3.3% Mannose
(% by weight).

In embodiments a polysaccharide for use in the present invention can have a sulphate content of about 17 to 35% by weight, 17 to 30% by weight, suitably, 25 to 30% by weight, suitably 17 to 25% by weight, suitably the polysaccharide may have a sulphate content of about 20% by weight, suitably about 19% by weight.

In embodiments a polysaccharide for use in the invention can demonstrate immunomodulatory activity in vitro, wherein for example the polysaccharide can inhibit neutrophil elastase activity by about 60 to 90%, in particular 60 to 80% relative to neutrophils to which the polysaccharide is not provided.

As well as being useful therapeutically to treat inflammatory conditions of the skin, it is considered embodiments of the polysaccharides described herein can be used to treat internal immune system disorders, in particular gut inflammatory conditions and respiratory conditions, for example gut inflammatory conditions including bowel disorders, irritable bowel syndrome, Crohn's disease, and ulcerative colitis and respiratory conditions including asthma, cystic fibrosis, emphysema, chronic obstructive pulmonary disorder, acute respiratory distress syndrome, or allergic rhinitis. Treatment of such conditions can be via ingestion of a polysaccharide or by inhalation of the polysaccharide. It is further considered that where a patient has an underlying immune system disorder, but no symptoms are present, then a polysaccharide as described herein may be provided to minimise the risk of symptoms.

Accordingly a second aspect of the present invention provides a nutritional supplement comprising a polysaccharide obtainable from *P. capsulatus* or a strain related to *P. capsulatus* wherein the gel forming polysaccharide is a sulphated heteropolymer, of molecular weight greater than 670 kDa, primarily comprising glucose, galactose, arabinose and uronic acid units.

Additionally, where no therapeutic benefit is required, the inventors consider that the polysaccharide may usefully provide cosmetic advantages for users.

Accordingly a third aspect of the invention is a cosmetic preparation comprising a polysaccharide obtainable from *Prasinococcus capsulatus* or a strain related to *P. capsulatus* wherein the gel forming polysaccharide is a sulphated heteropolymer of molecular weight greater than 670 kDa primarily comprising glucose, galactose, arabinose and uronic acid units.

As will be appreciated, the embodiments of the polysaccharide of the first aspect of the invention can be used in the second and third aspects of the invention.

Derivatives of Polysaccharide and their Use

The inventors have determined that derivatives of a gel forming polysaccharide obtainable from *Prasinococcus capsulatus* or a strain related to *P. capsulatus* wherein the gel forming polysaccharide is a sulphated heteropolymer of molecular weight greater than 670 kDa comprising glucose, galactose, arabinose and uronic acid units can also be used in the treatment of immune system disorders, in particular immune system disorders which promote an inflammatory response.

Accordingly a fourth aspect of the invention provides a derivative (oligosaccharide) of a gel forming polysaccharide from *Prasinococcus capsulatus* or a strain related to *P. capsulatus* wherein the gel forming polysaccharide is a sulphated heteropolymer of molecular weight greater than 670 kDa primarily comprising glucose, galactose, arabinose and uronic acid units wherein said derivative has a molecular weight in the range of about 2 kDa to 10 kDa, or in the range of about 2 to 20 kDa, or in the range of about 20 to 60 kDa.

As will be appreciated, embodiments of the polysaccharide of the first aspect of the invention can be used to form derivatives of the fourth aspect of the invention.

In embodiments a derivative can be a low molecular weight fragment with a molecular weight in the range 2 to 10 kDa. In embodiments a derivative can comprise a larger fragment of polysaccharide with a molecular weight in the range 20 to 60 kDa.

In embodiments low molecular weight fragments of the polysaccharide of around 2 to 10 kDa can comprise about
30 to 40% Glucose
30 to 40% Galactose
8 to 14% Arabinose
7 to 11% Uronic acid
and a small percentage (1 to 10%), suitably a small percentage (1 to 4%) of other sugar units (% by weight).

In embodiments low molecular weight fragments of the polysaccharide of around 2 to 10 kDa can comprise about
35% Glucose
35% Galactose
11% Arabinose
9% Uronic acid
and a small percentage (1 to 10%), suitably a small percentage (1 to 4%) of other sugar units (% by weight).

In embodiments a large fragment of the polysaccharide (around 20 to 60 kDa) can comprise
25 to 28% Glucose
35 to 55%, suitably 35 to 45% Galactose
8 to 17% Arabinose, suitably 15% Arabinose
4-6% Uronic acids
and a small percentage (1 to 4%) of other sugar units (% by weight).

In embodiments a large fragment of the polysaccharide (around 20 to 60 kDa) can comprise
25% Glucose
50% Galactose
15% Arabinose
5% Uronic acids
and a small percentage (1 to 5%) of other sugar units (% by weight).

In embodiments a derivative of a polysaccharide of the invention can comprise about
8.4% Arabinose
0.7% Rhamnose
2.0% Xylose
2.2% GalA (galacturonic acid)
57.9% Galactose
24.6% Glucose
3.8% GlcA (glucuronic acid)
by weight.

Suitably, in embodiments, a derivative of a polysaccharide of the present invention can have a sulphate content of about 20 to 30% by weight, suitably 25 to 30% by weight.

In embodiments an oligosaccharide derivative of the polysaccharide can inhibit neutrophil elastase release by about 70 to 90%, suitably 80 to 90% relative to neutrophils to which derivative is not provided In embodiments a derivative of the polysaccharide can inhibit neutrophil reactive oxygen species (ROS) production by about 30-40% relative to neutrophils in which derivative is not provided. In embodiments an oligosaccharide derivative can inhibit human keratinocyte IL-8 gene expression and release by about 70 to 100% relative to keratinocytes to which derivative is not provided. This activity compares to the well-characterised polysaccharide anticoagulant drug heparin, which inhibits elastase release by about 60-75% but which has no significant effect on ROS production. The activity also compares to the seaweed polysaccharide fucoidan, which inhibits elastase release by about 70 to 90%, and keratinocyte IL-8 release by about 80 to 90%.

In embodiments an oligosaccharide derivative of the polysaccharide can inhibit human keratinocyte IL6 and IL17C release by about 50-70% relative to human keratinocytes to which derivative is not provided. In embodiments an oligosaccharide derivative of the polysaccharide can inhibit the release of interferon gamma from human peripheral blood mononuclear cells (PBMCs) by about 50-70% relative to human PBMC's in which derivative is not provided. In embodiments an oligosaccharide can inhibit the chemotaxis of human neutrophils by about 50-70% and of THP-1 (monocyte) cells by about 30-50% relative to neutrophils and monocytes to which the derivative is not provided. In embodiments an oligosaccharide derivative of the polysaccharide can inhibit imiquimod induced mouse skin inflammation in a dose dependent manner relative to controls where the derivative is not provided.

By about is meant within 1 to 20%, more particularly within 10%, yet more particularly within 5%, even yet more particularly within 2% of the stated value.

Embodiments of derivatives of the invention can be for use in the treatment of immune system disorders, in particular immune system disorders which promote an inflammatory response, more specifically skin conditions, including eczema, psoriasis and atopic dermatitis.

Embodiments of derivatives of the invention can be for use in the treatment of internal immune system disorders, in particular gut inflammatory conditions and respiratory conditions, for example gut inflammatory conditions including bowel disorders, irritable bowel syndrome, Crohn's disease, and ulcerative colitis and respiratory conditions including asthma, cystic fibrosis, emphysema, chronic obstructive pulmonary disorder, acute respiratory distress syndrome, or allergic rhinitis.

The use of such derivatives in such treatments provides a further aspect of the invention.

Suitably embodiments of derivatives may be prepared by any method known in the art, including hydrolysis or enzymatic hydrolysis the polysaccharides or by free radical or photochemical methods, such as that described by Higashi et al (Controlled photochemical depolymerization of K5 heparosan, a bioengineered heparin precursor, Carbohydrate Polymers 86 (2011) 1365-1370).

Embodiments of derivatives of the invention can be depolymerised polysaccharides prepared by a free radical or photochemical method.

Embodiments of the derivatives can be oligosaccharides with a sulphate content of about 25-30% by weight.

Preferably an oligosaccharide derivative of the invention can have immunomodulatory properties equivalent or greater than the native polysaccharide material of the invention.

According to a fifth aspect of the invention there is provided a cosmetic preparation comprising at least one derivative of a polysaccharide from *Prasinococcus capsulatus* or a strain related to *P. capsulatus* wherein the gel forming polysaccharide is a sulphated heteropolymer of molecular weight greater than 670 kDa primarily comprising glucose, galactose, arabinose and uronic acid units wherein said derivative has a molecular weight in the range 2 kDa to 10 kDa or in the range of about 20 to 60 kDa.

In embodiments a derivative can be a low molecular weight fragment with a molecular weight in the range 2 to 10 kDa. In embodiments a derivative can comprise a large fragment of polysaccharide with a molecular weight in the range 20 to 60 kDa.

In embodiments, a combination of a large fragment of a derivative and low molecular weight fragment may be provided.

According to a sixth aspect of the invention there is provided a nutritional supplement comprising at least one derivative of a polysaccharide from *Prasinococcus capsulatus* or a strain related to *P. capsulatus* wherein the gel forming polysaccharide is a sulphated heteropolymer of molecular weight greater than 670 kDa primarily comprising glucose, galactose, arabinose and uronic acid units wherein said derivatives have a molecular weight in the range 2 kDa to 10 kDa or in the range of about 20 to 60 kDa.

In embodiments a derivative can be a low molecular weight fragment with a molecular weight in the range 2 to 10 kDa. In embodiments a derivative can comprise a large fragment of the polysaccharide with a molecular weight in the range 20 to 60 kDa.

In embodiments, a combination of a large fragment of a derivative and low molecular weight fragment may be provided.

Compositions

Suitably a polysaccharide or derivative as discussed herein can be provided as part of a composition. Such a composition may be suitable for oral, topical, rectal or parenteral, nasal or pulmonary administration (by inhalation). In embodiments the composition can be either for topical application to the skin or for ingestion according to use.

In embodiments a ready-for-use composition can be in the form of a tablet, capsule, cachet, or as a dispersible granule, which may be, for example, suspended in water before administration or sprinkled on food. A composition may conveniently be presented in unit dosage form and may be prepared by any of the methods well-known in the food industry for the preparation of food and food supplements, or by methods known to the pharmaceutical industry for use as a pharmaceutical, for example as a topical medication.

Compositions for topical administration may be provided, for example, as a gel, cream or ointment. Such compositions can be applied directly to the skin or carried on a suitable support, such as a bandage, gauze, mesh or the like that can be applied to an area to be treated.

Methods known to those skilled in the art of food manufacturing include, but are not limited to; dry-blending of active agents and other ingredients in powder form, spray-drying of emulsions containing all components or the use of extrusion technologies to form pellets or granules. Alternatively, the composition may be the form of a liquid tonic.

A polysaccharide or derivative may be provided as a pharmaceutically acceptable salt or pharmaceutically acceptable solvate. In embodiments the polysaccharide or derivative can be administered alone, or in admixture with a pharmaceutical carrier, excipient or diluent selected with regard to the intended route of administration and standard pharmaceutical practice. A pharmaceutical carrier can be a physiologically acceptable carrier, either organic or inorganic, natural or synthetic with which the polysaccharide or derivative thereof of the present invention can be combined to facilitate the application.

In embodiments a polysaccharide or derivative can be admixed with any suitable binder (s), lubricant (s), suspending agent (s), coating agent (s), solubilising agent (s), carrier(s), or buffer stabiliser(s).

A composition of the invention may also contain one or more further active compounds selected as necessary for the condition being treated. For example a composition may comprise a further active compound which targets distinct pathways or mechanisms from that targeted by the product of the invention. This may provide improved efficacy, for example a synergistic effect. In embodiments the polysaccharide or derivative can be provided in combination with Vitamin D.

Cosmeceutical or Cosmetic Preparation

In embodiments a polysaccharide or derivative of the present invention can be provided as a cosmeceutical, i.e. a cosmetic product with biologically active ingredients purporting to have medical or drug like benefits.

Alternatively, a polysaccharide or derivative of the present invention can be provided as a cosmetic which improves the appearance and function of the skin, but does not have a clinical effect.

Suitably, compositions for use as a cosmeceutical or cosmetic preparation can be provided as known in the art, including, but not limited to skin creams, gels, serums, washes, rinses, shampoos, conditioners, mousses and the like.

Embodiments of a cosmetic preparation of the invention can be provided for example as a cream, serum, gel or ointment for topical administration to the skin. In embodiments the cosmetic preparation can be for use as an anti-aging skin preparation, for use in skin toning/smoothing or to alter the colour of the skin. Such preparations may suitably minimise effects considered to be related to aging such as the visual appearance of wrinkles, sun-damage and may increase skin elasticity. In such cosmetic compositions the polysaccharide or derivative thereof can typically be provided in combination with a base carrier or skin moisturising substance. Suitably a base carrier is compatible with the other ingredients of the composition and not deleterious to the user of the cosmetic. Typically such preparations may further include preservatives, fragrance or anti-oxidants. Additionally, such preparations may include water, wetting agents, alcohols, oils, colourants and the like.

In embodiments a cosmetic preparation can be provided comprising a polysaccharide for use in the invention. In preferred embodiments a cosmetic preparation can be provided with a derivative as discussed herein.

Nutritional Supplement

In embodiments a nutritional supplement of the invention can promote a healthy gut in the subject which receives the nutritional supplement. Suitably embodiments of a nutritional supplement can decrease cramping or discomfort in the bowel. In embodiments a nutritional supplement can be provided comprising a polysaccharide for use in the invention. In preferred embodiments a nutritional supplement can be provided with a derivative as discussed herein.

In embodiments a nutritional supplement of the invention can be formulated in capsule form to be taken orally. In embodiments a nutritional supplement can be provided as part of a neutraceutical composition.

Preparation of a Polysaccharide

In embodiments, a polysaccharide for use in the invention or derivatives of such a polysaccharide can be a polysaccharide isolated from the cellular or secreted fraction of a culture of *Prasinococcus capsulatus* or a strain related to *P. capsulatus*.

In embodiments the polysaccharide for use in the invention or at least one derivative of such a polysaccharide can be isolated from the cellular fraction of a culture of *Prasinococcus capsulatus* or a strain related to *P. capsulatus*.

In embodiments the polysaccharide for use in the invention or at least one derivative of such a polysaccharide can be isolated from the secreted fraction of a culture of *Prasinococcus capsulatus* or a strain related to *P. capsulatus*.

In embodiments, a culture of *Prasinococcus capsulatus* can be the *Prasinococcus capsulatus* algal strain CCMPII94. This algal strain is publicly available. The culture can be suitably grown in algal culture media as would be known in the art wherein modifications of the nitrogen, vitamin, silica or trace metals provided in the algal media may be made as would be known to one of skill in the art. The algal culture medium can be used with a sea water base or using synthetic sea water.

In embodiments a f/2 growth medium can be used with the following composition:

Stock Solutions:

| Trace elements: | g/Liter | Vitamin mix: | g/Liter |
|---|---|---|---|
| $Na_2EDTA \cdot 2H_2O$ | 4.16 | Vitamin $B_{12}$ (cyanocobalamin] | 0.0005 |
| $FeCl_3 \cdot 6H_2O$ | 3.15 | Thiamine HCl (Vitamin $B_1$) | 0.1 |
| $CuSO_4 \cdot 5H_2O$ | 0.01 | Biotin | 0.0005 |
| $ZnSO_4 \cdot 7H_2O$ | 0.022 | | |
| $CoCl_2 \cdot 6H_2O$ | 0.01 | | |
| $MnCl_2 \cdot 4H_2O$ | 0.18 | | |
| $Na_2MoO_4 \cdot 2H_2O$ | 0.006 | | |

Such culture media is discussed by Sieburth, et al. Widespread occurrence of the oceanic ultraplankter, *Prasinococcus capsulatus* (prasinophyceae), the diagnostic "golgi-decapore complex" and the newly described polysaccharide "capsulan". J. Phycol. 35, 1032-1043 (1999) and Guillard R. and Ryther J. 1962 Studies of marine planktonic diatoms. Can. J. Microbiol. 8: 229-239.

Suitable medium can be made by adding the following to 950 mls filtered sea water (salinity 29-32 ppt).

Medium:

| | g/Liter |
|---|---|
| $NaNO_3$ | 0.075 |
| $NaH_2PO_4 \cdot 2H_2O$ | 0.00565 |
| Trace element stock solution | 1 mL |
| Vitamin mix stock solution | 1 mL |

Typically the pH can be set to 8.0 (2 ml 1M Tris-HCl at pH8 per liter of medium) and media made up to 1 liter with sea water. Medium can be sterilised by autoclaving (eg. 121° C., 15 mins) and stored at 2-8° C.

Variations for *P. capsulatus* culture can be used wherein 80% of $NaH_2PO_4.2H_2O$ as above is used, plus 100 mg sodium glycerophosphate/liter and wherein the twice the concentration of $NaNO_3$ and vitamins is included to increase biomass.

According to a further aspect of the present invention, there is provided a method to produce the polysaccharide for use in the invention or a derivative of the polysaccharide wherein the method comprises the steps:

culture of microalgae, suitably a culture of *Prasinococcus capsulatus*, in particular the *Prasinococcus capsulatus* algal strain CCMPII94, separation of microalgal biomass from culture medium, concentration and desalting of the culture medium and drying of the culture media.

Suitably, separation of the microalgae biomass from the medium may be by centrifugation. In alternative embodiments separation may suitably be performed by filtration, flocculation, or tangential flow filtration. Suitably concentration may be by tangential flow filtration. In embodiments this may be by using a 100 kDa membrane. This may allow desalting of the medium if diafiltration is also carried out.

Suitably, separation of the polysaccharide from the medium may be provided by precipitation, dialysis, tangential flow filtration and/or ion exchange chromatography In embodiments, separation is provided by ion exchange chromatography and concentration by tangential flow filtration.

After separation the media fraction may be dried. Drying may be performed using, for example, lyophilisation and heat drying, shelf drying using reduced atmospheric pressure or vacuum to dry at room temperature (20 degrees C.), spray drying, rotary drying, or spin flash drying.

Suitably drying may be by spray drying of concentrated and desalted medium.

The cells (cell pellets) can also be processed to extract the target polysaccharide, for example the step of extracting may be a step of hot water extraction or an enzymatic digest step or another suitable extraction protocol.

Extraction may be performed using for example, pressure disruption, ball milling, sonication, or blending (high speed or Waring).

In preferred embodiments the method can provide a derivative(s) of the polysaccharide wherein the derivatives are prepared by depolymerisation of the native polysaccharide by a free-radical or photochemical method, followed by fractionation using size exclusion chromatography or tangential flow chromatography to produce oligosaccharide fractions of defined molecular weight.

Treatment

A polysaccharide, a derivative thereof or a composition containing the polysaccharide or a derivative thereof may be used to treat a number of medical conditions. Treatment includes any regime that can benefit a human or non-human animal. The treatment may be in respect of an existing condition or may be prophylactic (preventative treatment). Treatment may include curative, alleviation or prophylactic effects.

Suitably a polysaccharide, a derivative thereof or a composition containing the polysaccharide or a derivative thereof may be provided as a tablet or capsule. Suitably, a polysaccharide, a derivative thereof or a composition containing the polysaccharide or a derivative thereof may be administered in a sustained release formulation. Suitably the polysaccharide, a derivative thereof or a composition containing the polysaccharide or a derivative thereof can be provided as a dietary supplement to an animal, including humans, that will provide a protective benefit to the animal and/or to be used therapeutically to modulate the immune response, in particular to modulate the inflammatory response, of the animal in particular a human.

Administration

The invention provides a polysaccharide for use or a derivative of the present invention, or a composition containing the same, for use as a medicament. The medicament may be for human usage or veterinary usage. Suitably in veterinary usage the animal patient may be a terrestrial animal, more suitably a companion or performance animal. Suitably a patient may be a human. Suitably, a derivative of the polysaccharide or a composition containing the polysaccharide or a derivative thereof can be applied topically to the patient, e.g. applied to the skin.

The product of the present invention may be administered by oral, topical, rectal or parenteral, nasal or pulmonary (by inhalation) routes. Typically, the physician will determine the actual dosage which will be most suitable for an individual patient and it will vary with the age, weight and response of the particular patient. In general, a therapeutically effective daily oral dose of the product of the invention is likely to range from 1 to 50 mg/kg body weight of the subject to be treated, preferably 10 to 20 mg/kg. The above dosages are exemplary of the average case. There can, of course, be individual instances where higher or lower dosage ranges are merited, and such are within the scope of this invention.

Accordingly, there is provided a method of administration of the polysaccharide of the first aspect of the invention or a derivative of the fourth aspect of the invention for the treatment of disorders of the immune system, in particular inflammatory conditions, more particularly inflammatory conditions of the skin, including eczema, psoriasis and atopic dermatitis and/or internal immune system disorders, in particular gut inflammatory conditions and respiratory conditions, for example gut inflammatory conditions including bowel disorders, irritable bowel syndrome, Crohn's disease, and ulcerative colitis and respiratory conditions including asthma, cystic fibrosis, emphysema, chronic obstructive pulmonary disorder, acute respiratory distress syndrome, or allergic rhinitis wherein the method comprises providing a therapeutically effective amount of the polysaccharide and/or derivative to a subject in need thereof.

Preferred features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness. Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

BRIEF DESCRIPTION OF THE DRAWINGS

Embodiments of the present invention will now be discussed by way of example only with reference to the figures in which:

FIG. 3e illustrates a table of example data from the monosaccharide analysis of *P. capsulatus* polysaccharide and polysaccharide derivatives comparing the methanolysis—GC-FID method with a TFA-hydrolysis—HPAEC-PAD method wherein repeat samples of the small polysaccharide derivatives (2-10 kDa) and the HMW native polysaccharide represent different preparations. Data shown as % monosaccharide composition. Both methods show the presence of similar monosaccharides although percentages vary. Example data from the TFA/HPAEC-PAD method shows the presence of galactose in all samples, although at a lower percentage than the methanolysis-TMS GC-FID method. This could be due to the stronger acid conditions (TFA) used for hydrolysis.

43-61 minutes=large fragment derivatives (20-60 kDa),
61-81 minutes=small fragment derivatives (2-10 kDa).

Material eluting after 100 minutes (co-eluting with the salt peak—green (iii)) are monosaccharides.

Figure 1A:
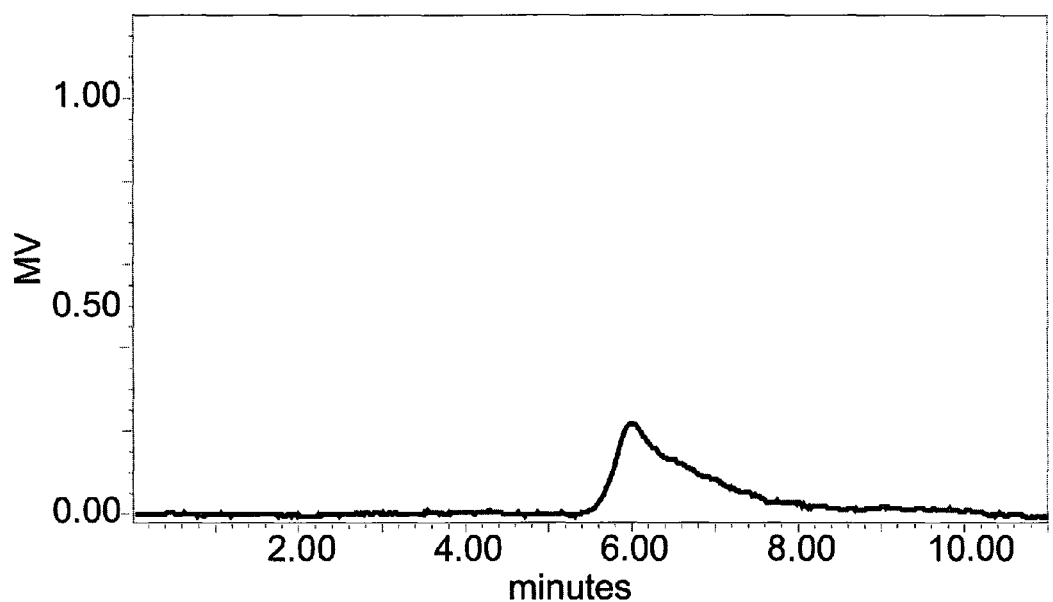
FIGS. 1a and b illustrate example HPLC-size exclusion chromatograms of *P. capsulatus* polysaccharide showing purity and molecular weight, wherein (a) is an example chromatogram from the HPLC-size exclusion analysis of polysaccharide using refractive index detection and the sample is above the resolution of the Biosep 4000 column (top standard 670 kDa) and (b) is example chromatograms and contour plot from the size exclusion analysis of polysaccharide using photodiode array detection wherein sample is above the resolution of the Biosep 4000 column used. Minimal absorbance at low wavelength only.
Figure 1B:
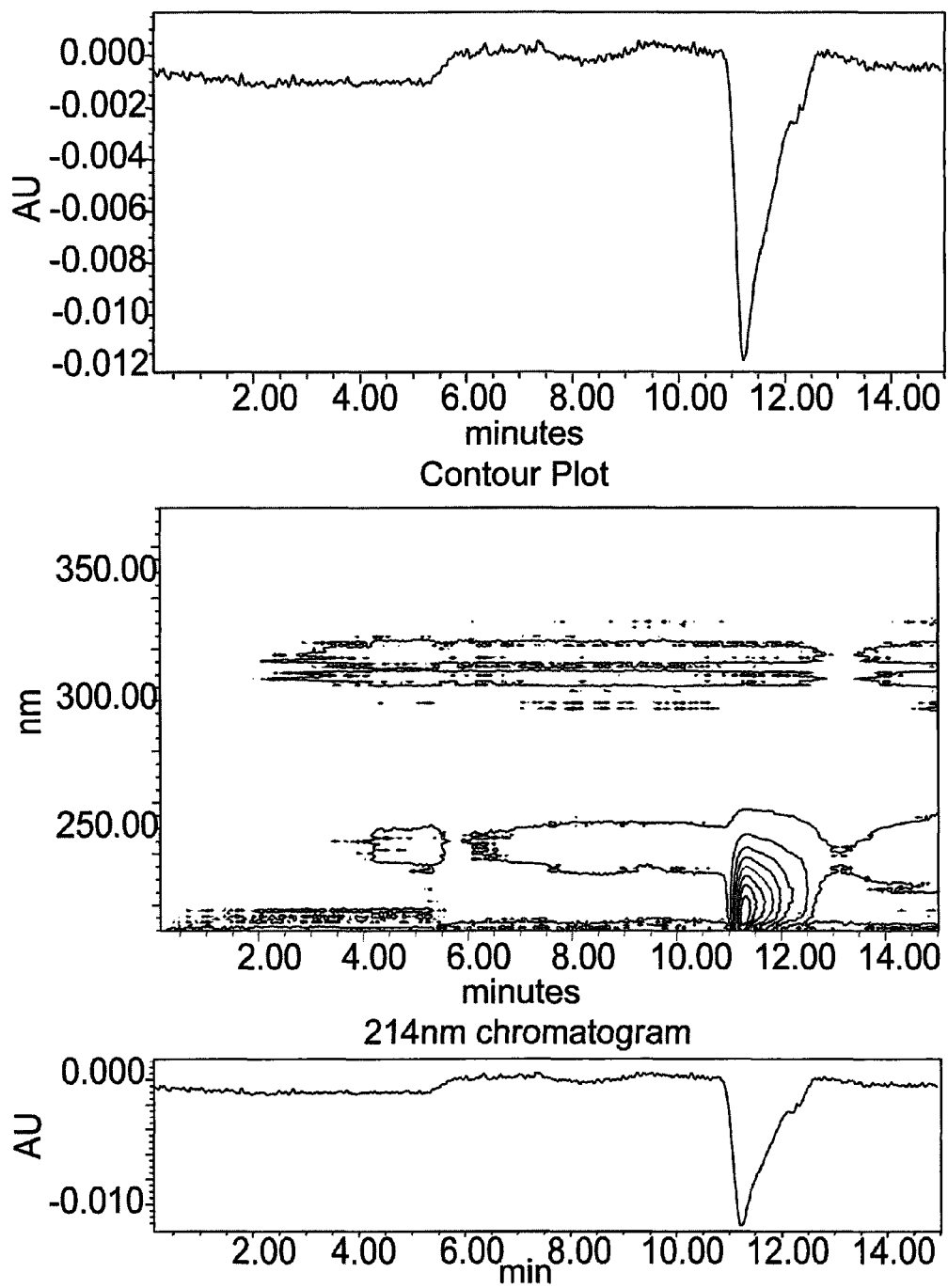
Figure 2A:
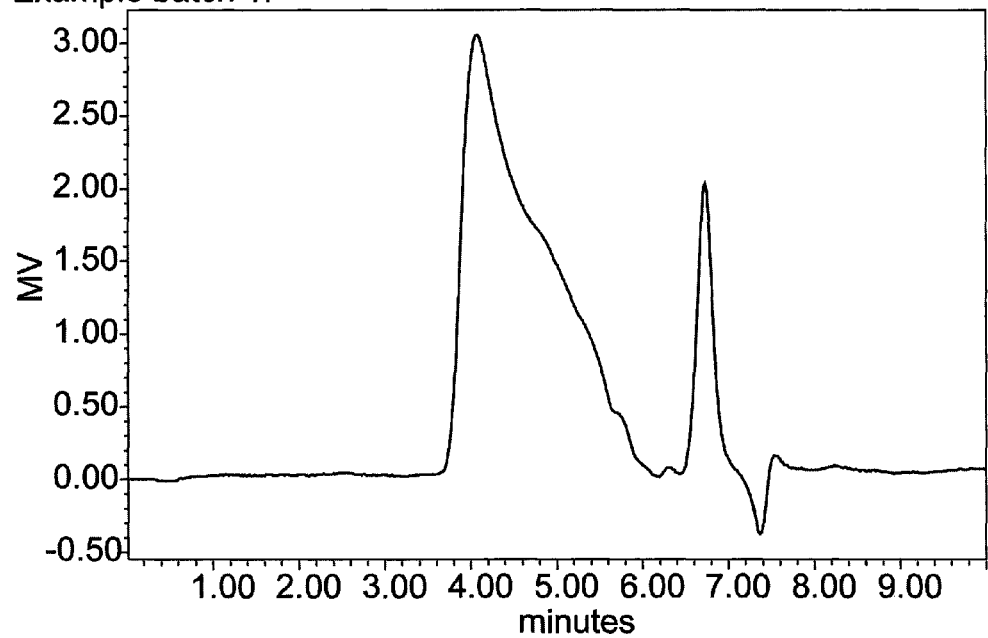
FIGS. 2a and b illustrate two example HPLC-size exclusion chromatograms of *P. capsulatus* polysaccharide derivatives showing purity and molecular weight based on using refractive index detection, YMC120 Diol column and peaks after 6.5 minutes are associated with the mobile phase buffer. Example batches indicate good reproducibility of process and 1→8 kDa range of LMW material.
Figure 2B:
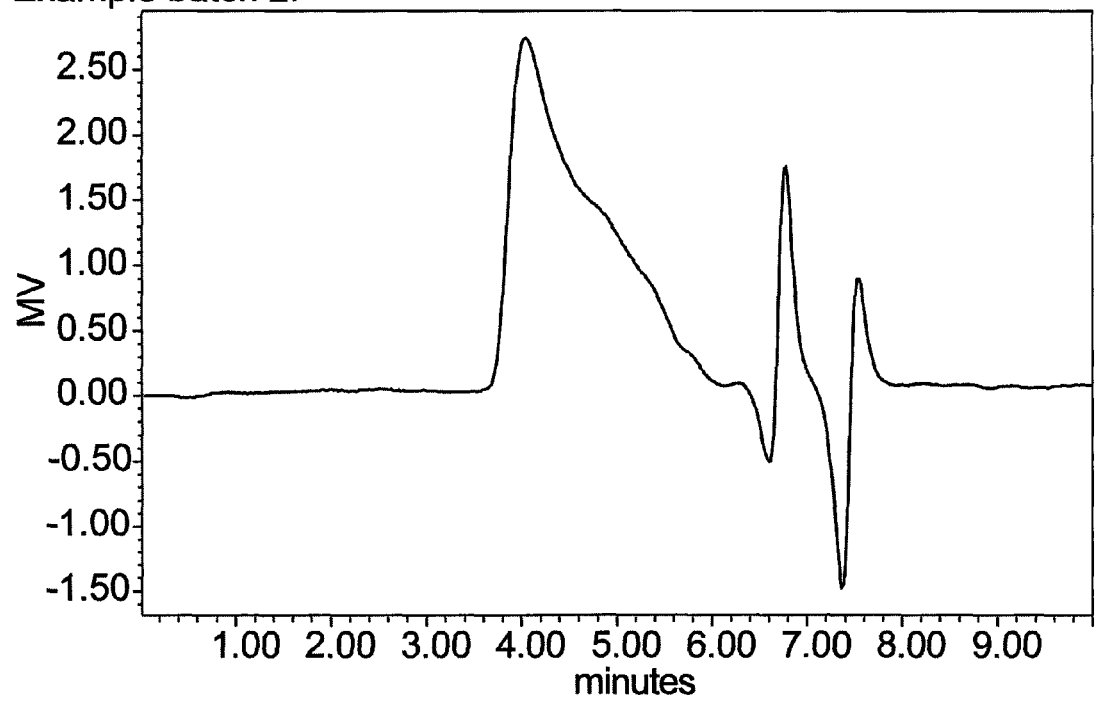
Figure 3A:
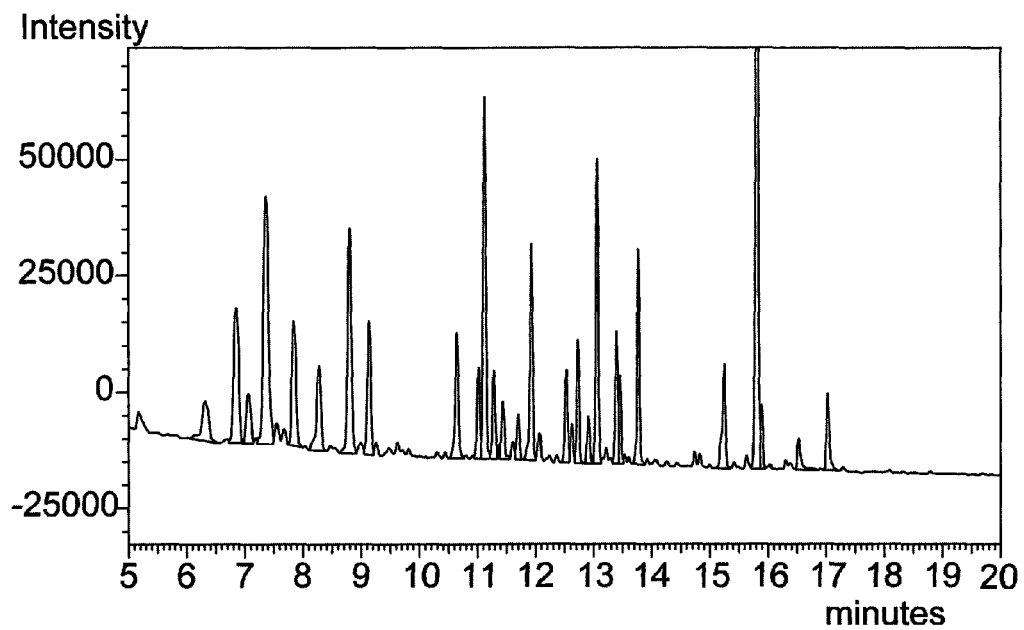
FIGS. 3a, 3b, 3c and 3d illustrate example chromatograms from the monosaccharide analysis of *P. capsulatus* polysaccharides and polysaccharide derivatives using methanolysis-TMS derivatisation GC-FID method, wherein (a) is an example chromatogram of the mixed monosaccharide standards used in the methanolysis—TMS GC-FID method with tabulated data below; (b) is an example chromatogram from the monosaccharide analysis of *P. capsulatus* polysaccharide showing the key monosaccharide peaks, based on comparison with mixed standards and internal standard ratio with tabulated data below; (c) is an example chromatogram from the monosaccharide analysis of polysaccharide derivatives (large polysaccharide fragment 20-60 kDa), showing the key monosaccharide peaks, based on comparison with mixed standards and internal standard ratio with tabulated data below; (d) is an example chromatogram from the monosaccharide analysis of polysaccharide derivatives (small polysaccharide fragment 2-10 kDa), showing the key monosaccharide peaks, based on comparison with mixed standards and internal standard ratio with tabulated data below.
Figure 3B:
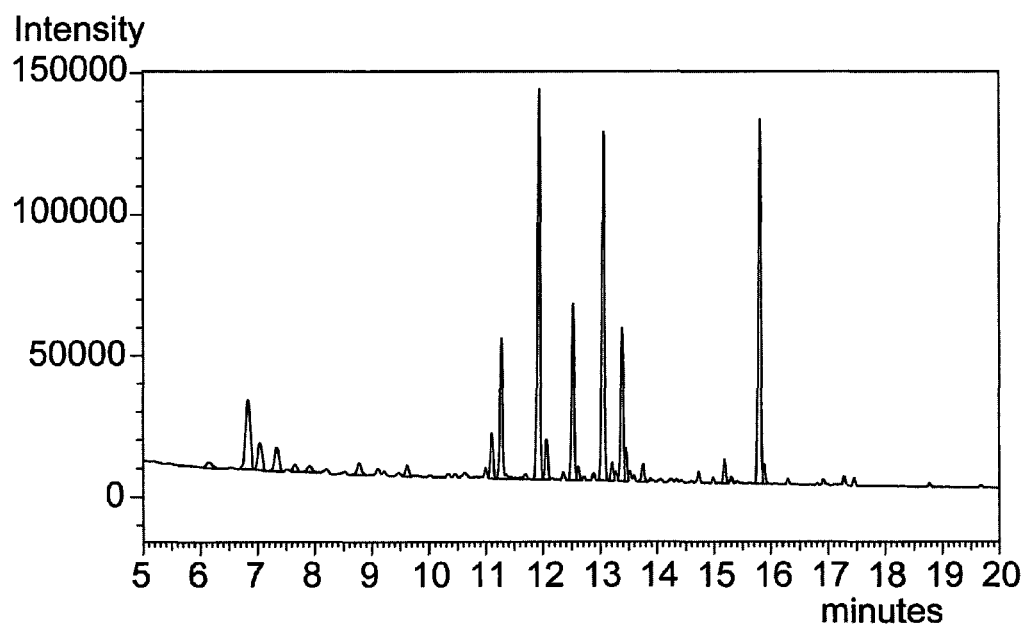
Figure 3C:
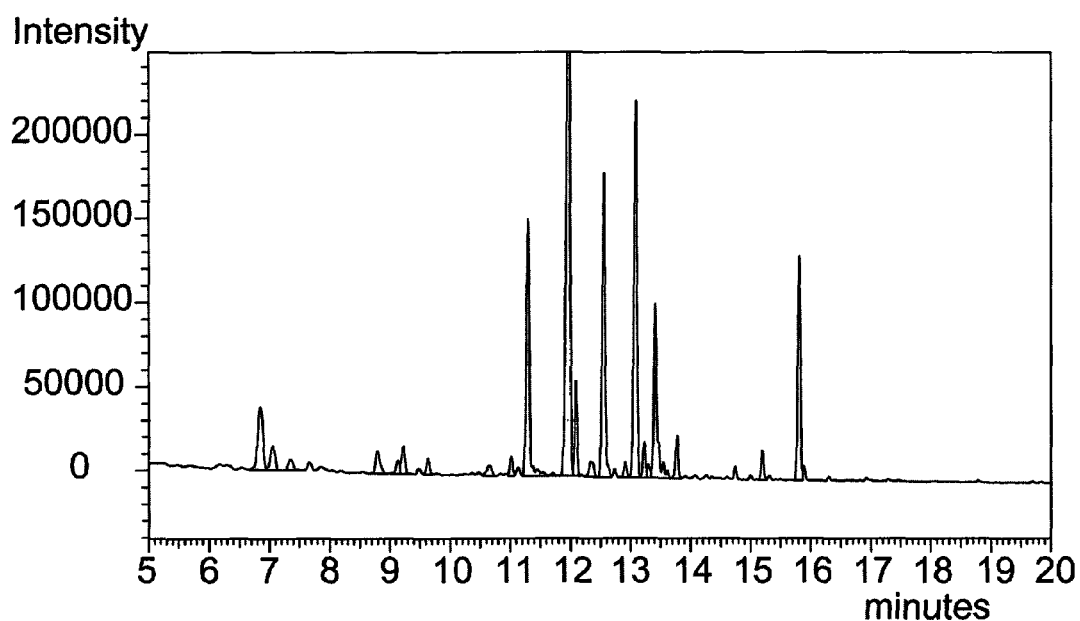
Figure 3D:
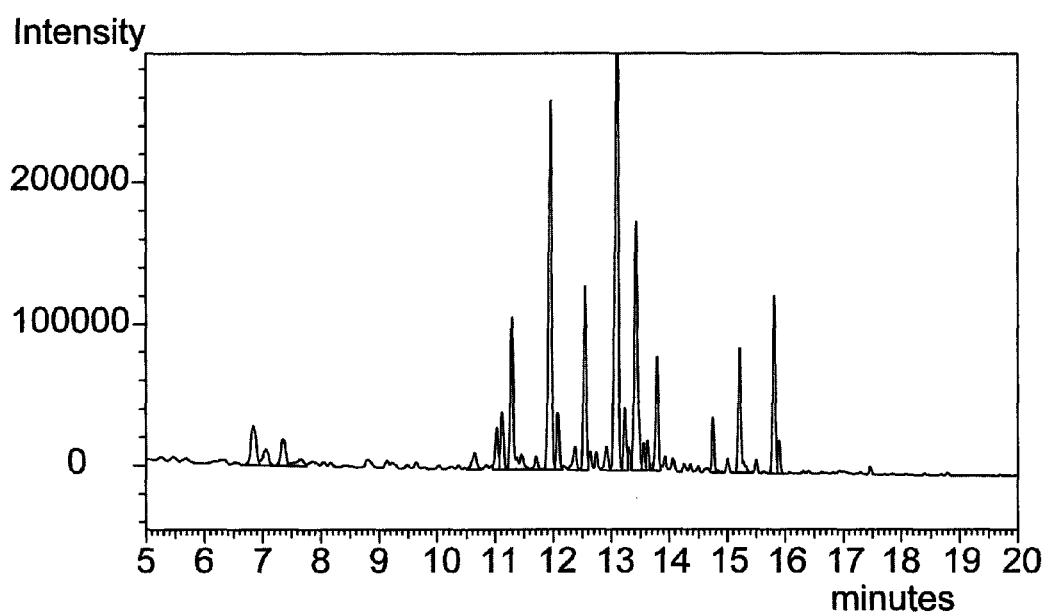
Figure 3F:
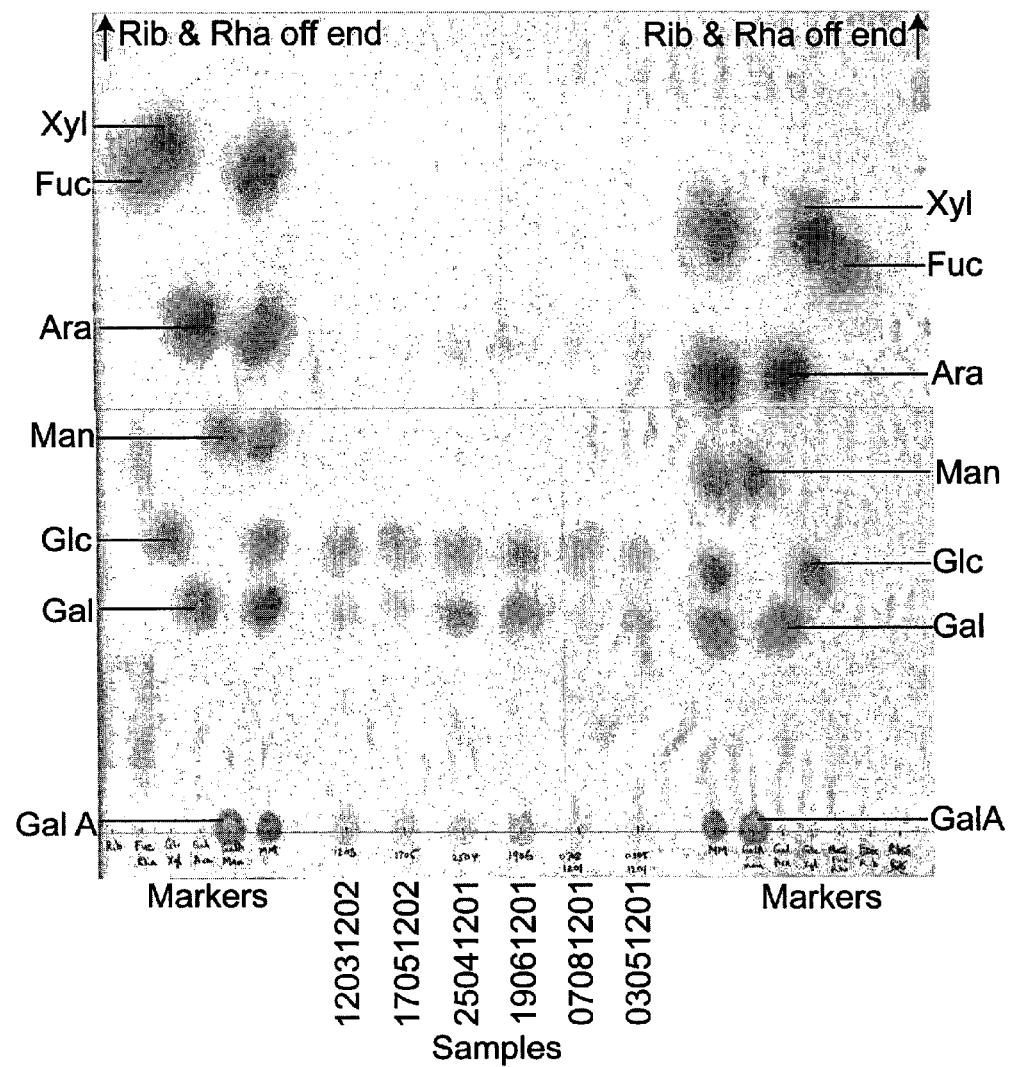
FIGS. 3f and g illustrate example paper chromatograms of TFA treated hydrolysates of *P. capsulatus* polysaccharide and polysaccharide derivatives to determine monosaccharide composition wherein (f) illustrates example results from paper chromatography of *P. capsulatus* polysaccharide hydrolysates from TFA-HPAEC monosaccharide analysis method (data shown in FIG. 3e) illustrating monosaccharide composition. Each marker is 25 μg. Solvent ethyl acetate:pyridine:water 8:2:1 Stain: aniline hydrogen-phthalate (where Xyl=xylose, Fuc=fucose, Ara=arabinose, Man=mannose, Glc=glucose, Gal=galactose, GalA=galacturonic acid, Rib=ribose, Rha=rhamnose, Samp=*P. capsulatus* polysaccharide sample). The major monosaccharides identified in the *P. capsulatus* polysaccharide and polysaccharide derivatives, support the data shown in FIG. 3b-e.
Figure 3G:
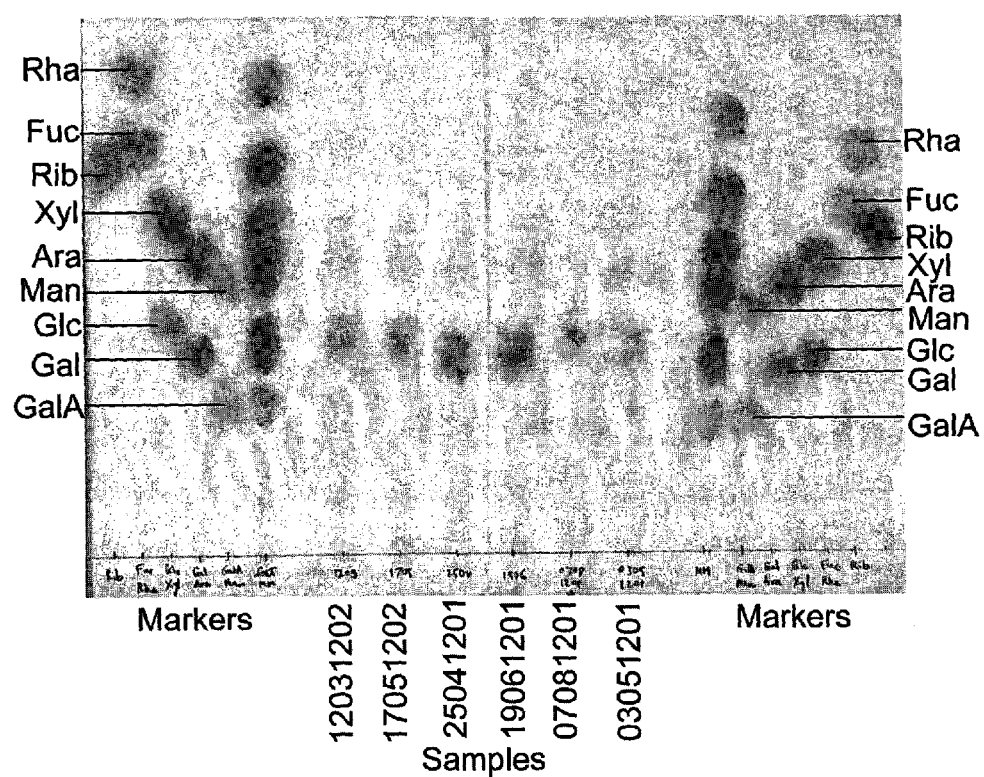
FIG. 3g illustrates example results from paper chromatography of *P. capsulatus* hydrolysates from TFA—HPAEC monosaccharide analysis method (FIG. 3e) illustrating monosaccharide composition. Each marker is 25 μg. Solvent butanol:acetic acid:water 12:3:5 Stain: aniline hydrogen-phthalate (where Xyl=xylose, Fuc=fucose, Ara=arabinose, Man=mannose, Glc=glucose, Gal=galactose, GalA=galacturonic acid, Rib=ribose, Rha=rhamnose, Samp=*P. capsulatus* polysaccharide sample). The major monosaccharides identified in the *P. capsulatus* polysaccharide and polysaccharide derivatives, support the data shown in FIG. 3b-f.
Figure 4:
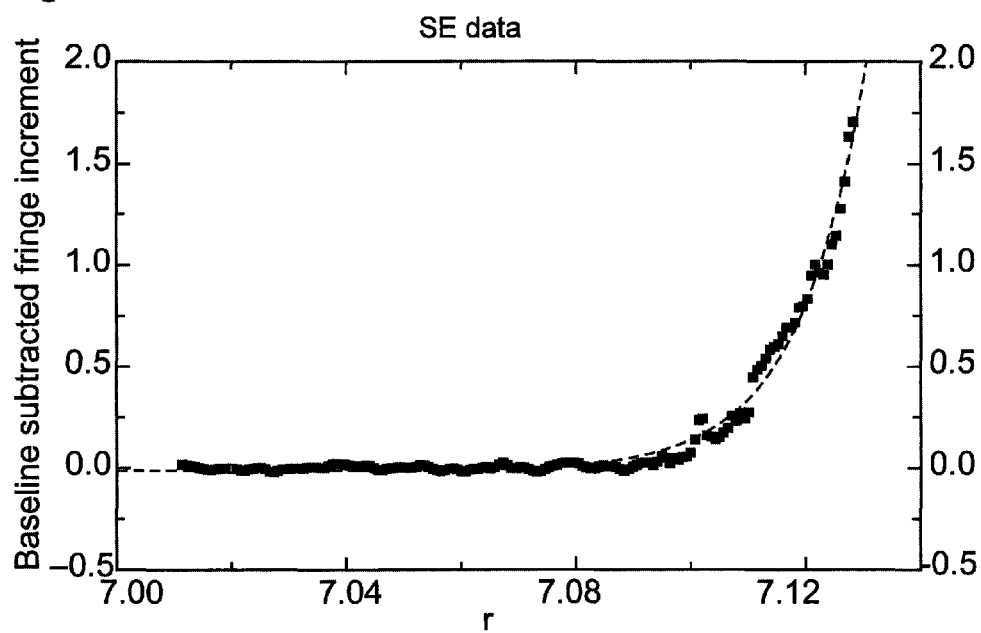
FIG. 4 illustrates example molecular weight estimation of *P. capsulatus* polysaccharide using sedimentation equilibrium wherein an example calculation of approximate molecular weight of the *P. capsulatus* native polysaccharide using sedimentation equilibrium techniques is provided. Sample was run at 0.5 mg/ml in 0.1M NaCl. Sedimentation velocity experiment was carried out to assess heterogeneity, before molecular weight analysis by sedimentation equilibrium. Data fit was achieved at a rotor speed of 1400 rpm with 1 mm column. *P. capsulatus* native polysaccharide was calculated to have a molecular weight of 38.62 Mega Daltons.
Figure 5:
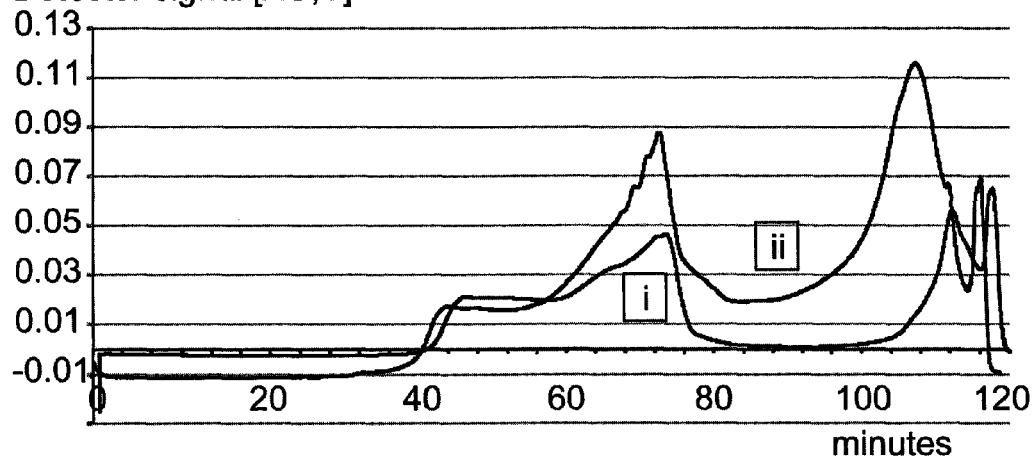
FIG. 5 illustrates an example size exclusion chromatogram showing the purification of *P. capsulatus* polysaccharide derivatives after free-radical depolymerisation. Size exclusion chromatography purification was using (Superdex 30 resin) and desalting of *P. capsulatus* polysaccharide derivatives after depolymerisation. Absorbance at 214 nm (light blue) (i), A280 (dark blue (ii)) (top panel) and conductivity (green) (iii) (lower panel) monitored. 3 ml fractions collected from 30 mins onwards, with 3 ml delay between UV monitor and fraction collector. Two broad size ranges can be seen in the main peaks and these were collected.
Figure 5:
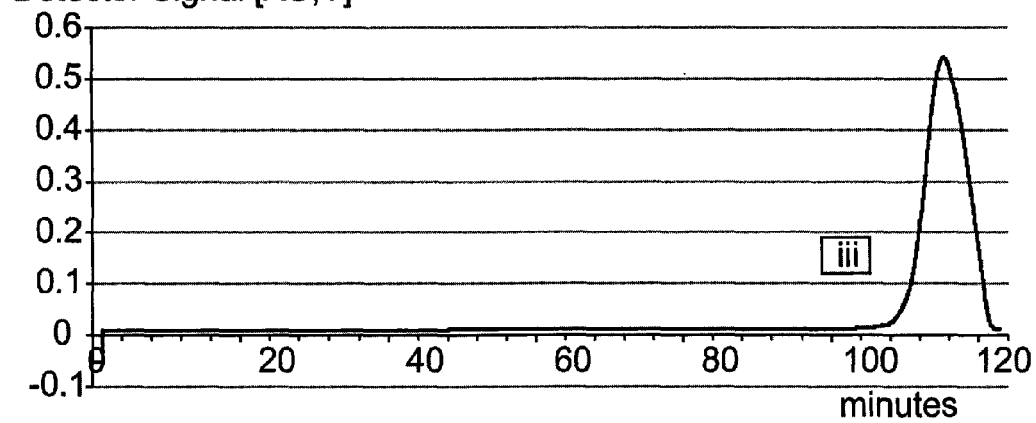
Figure 6:
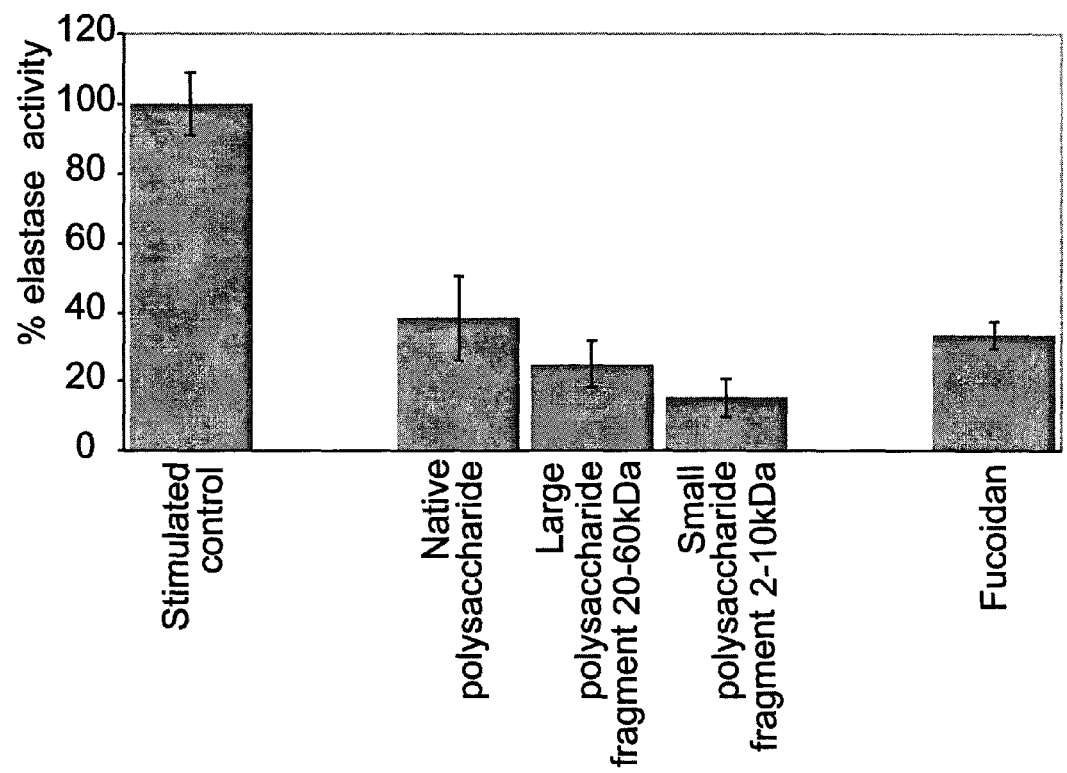

FIG. 6 illustrates the effects of *P. capsulatus* polysaccharide, and derivatives of polysaccharide, on human neutrophil elastase activity wherein there is shown example data for the effects of *P. capsulatus* polysaccharide, and polysaccharide derivatives on human neutrophil elastase activity (all samples at 0.1 mg/ml). Data illustrates the mean elastase activity±SD, % relative to control, from several batches of product. Treatment with algal polysaccharide and derivatives results in a reduction of elastase activity.

Figure 7:
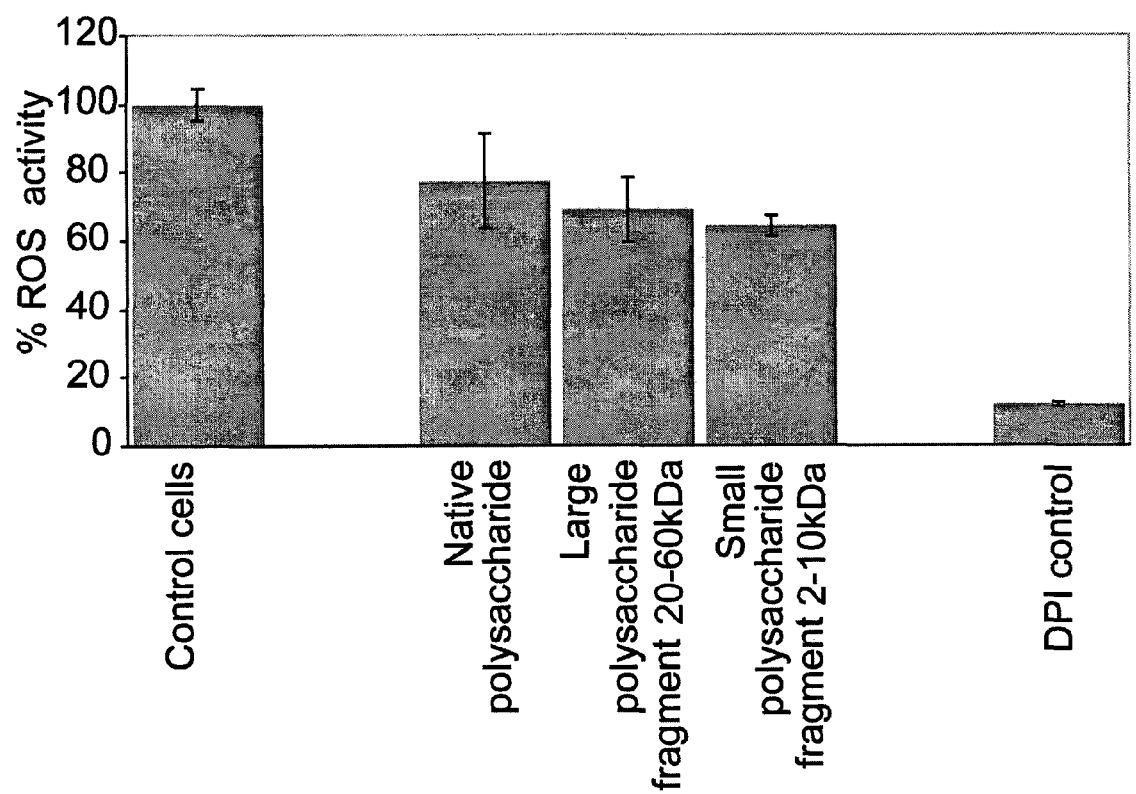

FIG. 7 illustrates the effects of *P. capsulatus* polysaccharide, and derivatives of polysaccharide, on human neutrophil ROS production wherein there is shown example data for the effects of *P. capsulatus* polysaccharide, and polysaccharide derivatives on human neutrophil reactive oxygen species (ROS) production (all samples at 0.1 mg/ml). Data illustrates the mean ROS signal±SD, % relative to control, from several batches of product. Treatment with algal polysaccharide and derivatives results in reduction of ROS.

Figure 8:
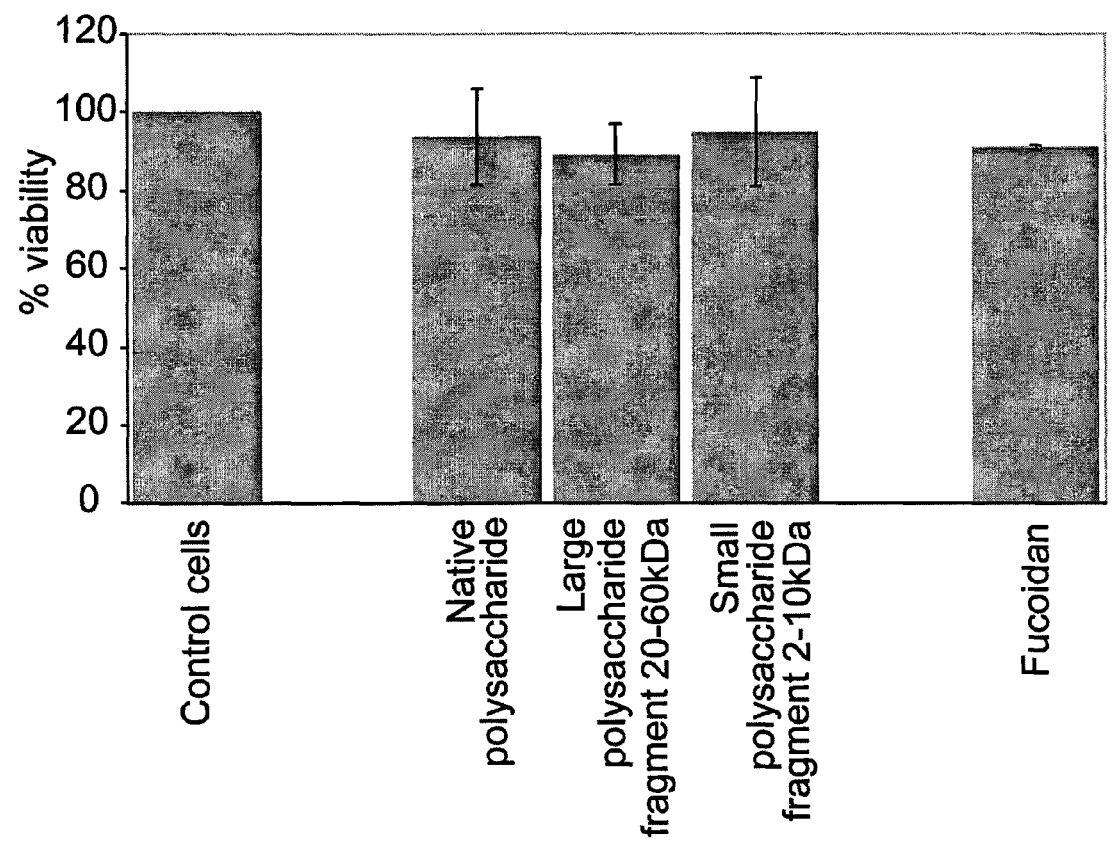

FIG. 8 illustrates the effects of *P. capsulatus* polysaccharide, and derivatives of polysaccharide on BHK cell viability wherein there is provided example data for the effects of *P.* capsulatus polysaccharide and polysaccharide derivatives on BHK cell viability (all samples at 0.1 mg/ml). The data illustrates the mean cell viability±SD, % relative to control, from several batches of product. Treatment with algal polysaccharide and derivatives results in no effects on observed cell viability.

Figure 9A:
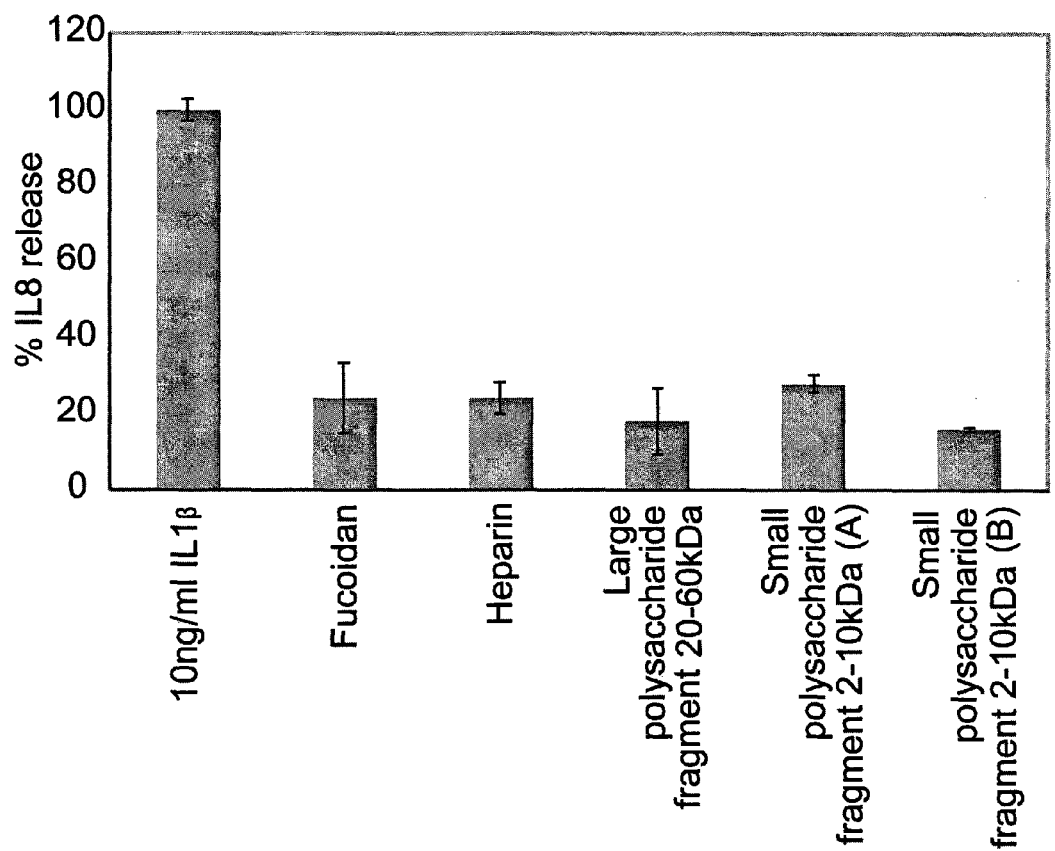
Figure 9B:
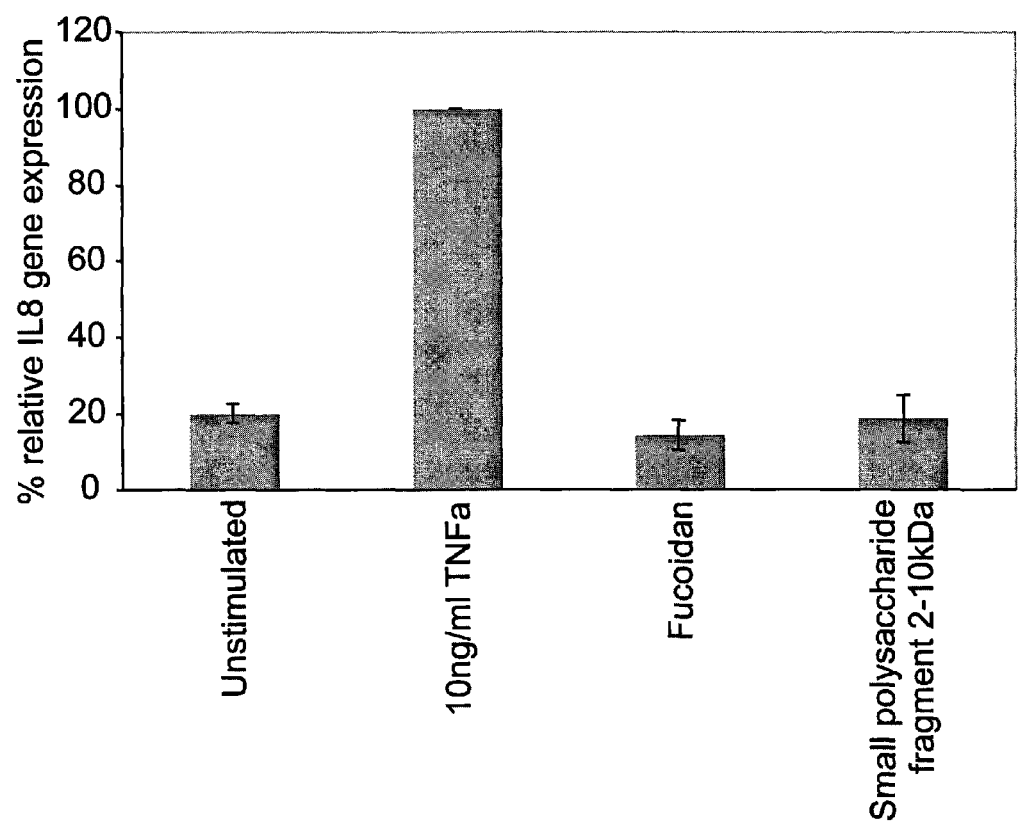
Figure 10:
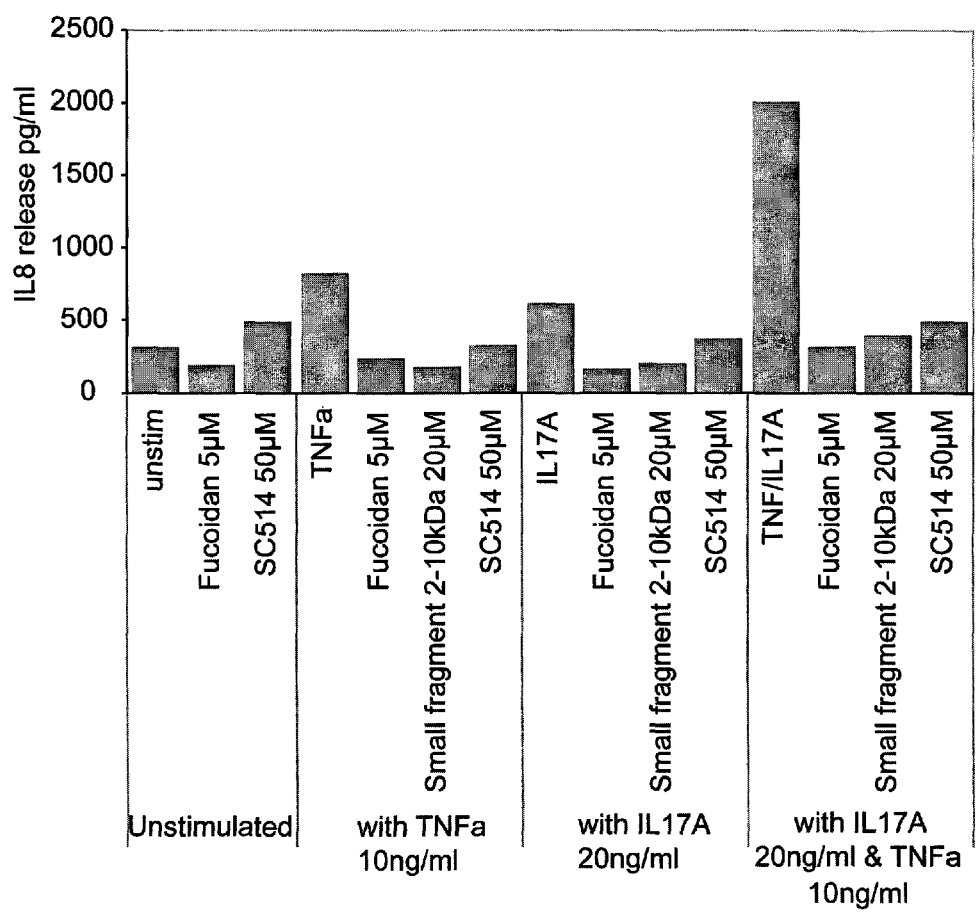
Figure 11A:
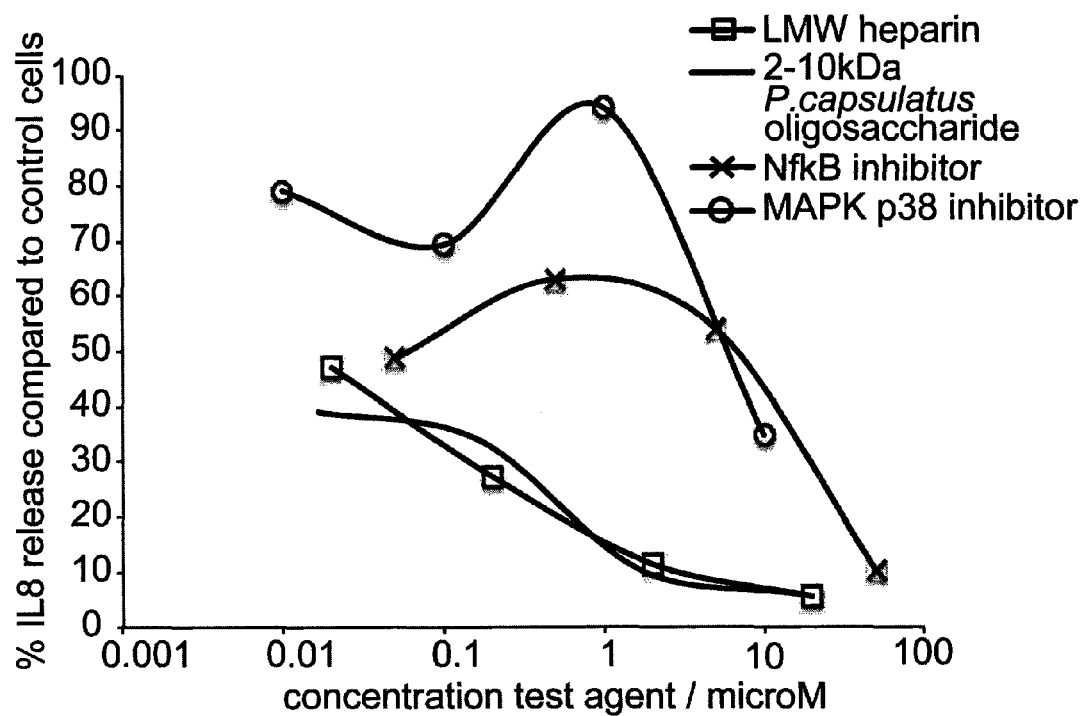
Figure 11B:
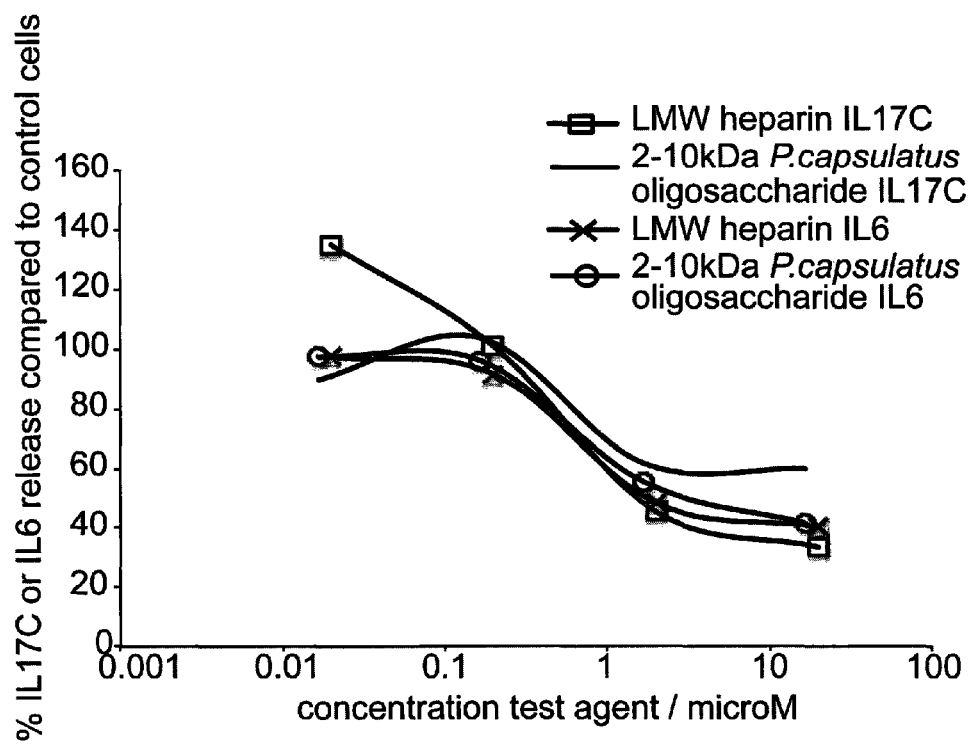
Figure 12:
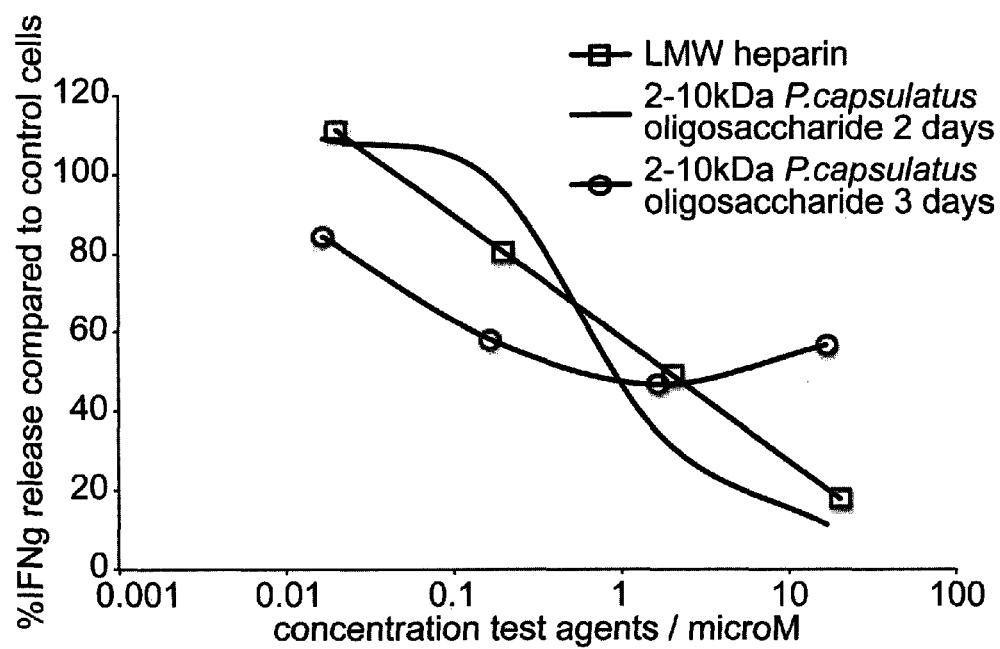
Figure 13:
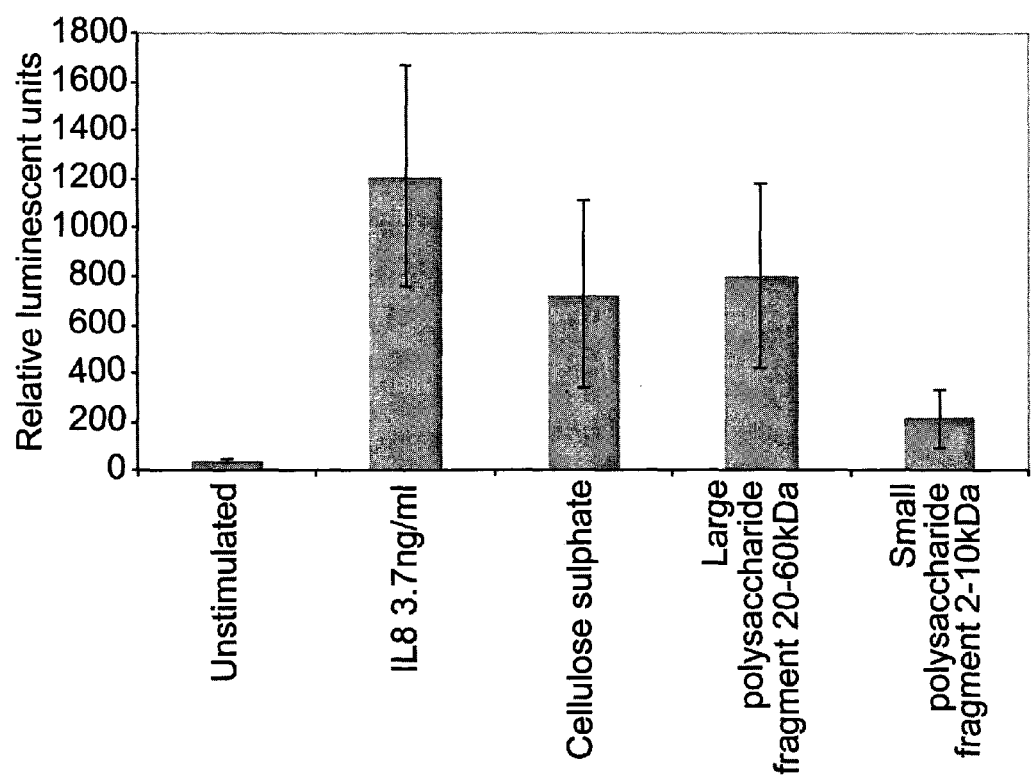
Figure 14:
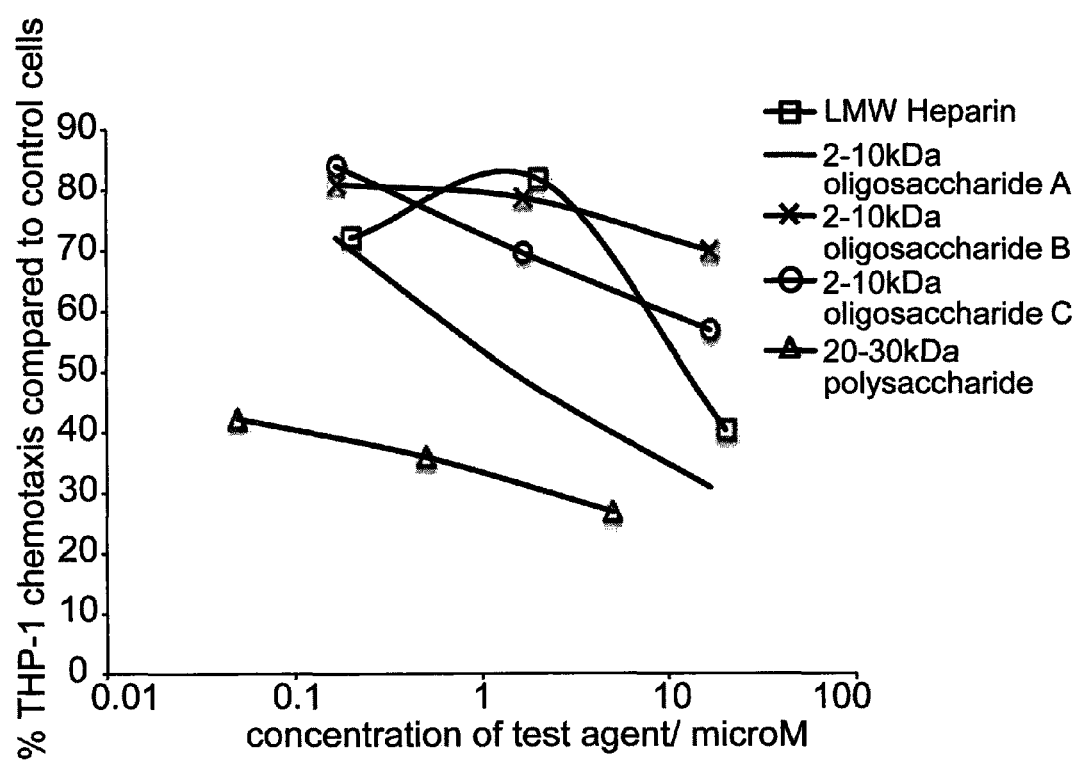
Figure 15:
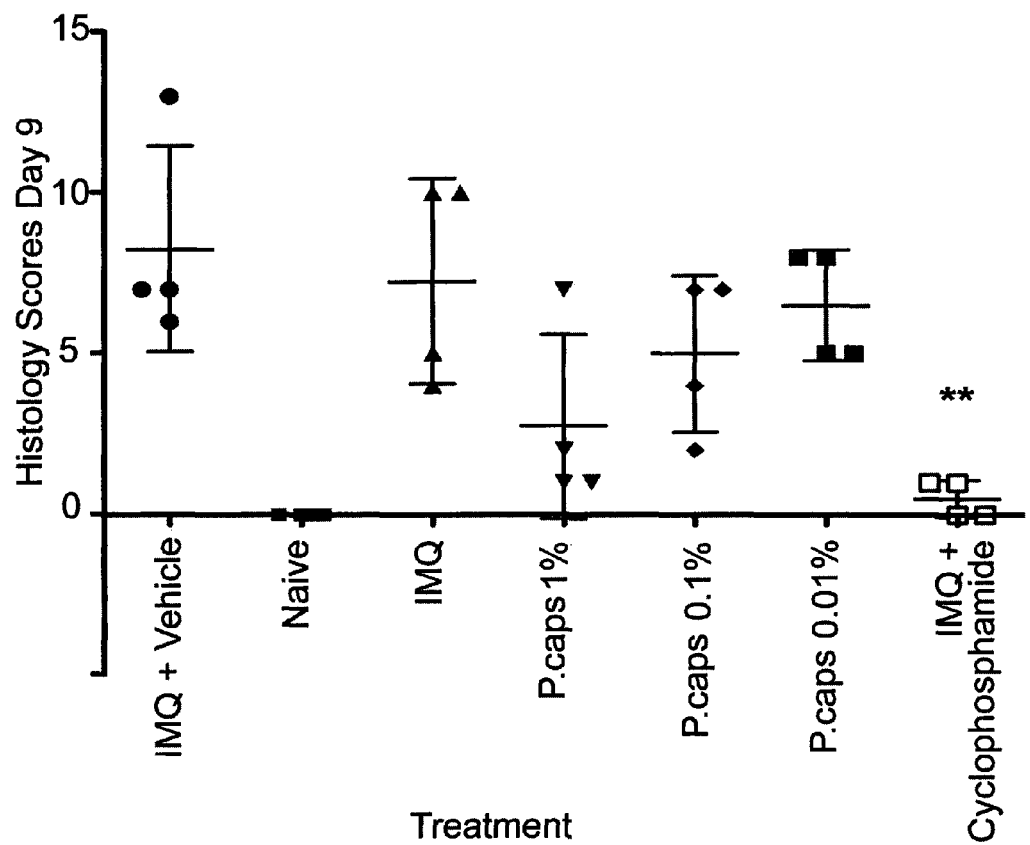

FIGS. 9a and 9b illustrates the effects of *P. capsulatus* polysaccharide derivatives on IL8 release or IL8 gene expression by primary human keratinocytes after stimulation with 10 ng/ml of IL1beta or 10 ng/ml TNFalpha wherein (a) is Example data for the effects of *P. capsulatus* polysaccharide and polysaccharide derivatives on IL8 release from primary human keratinocytes after stimulation with 10 ng/ml of IL1beta (all samples at 0.1 mg/ml). The data illustrates the % release±SD, relative to the IL1beta only control. Fucoidan and heparin treatments are run for comparison. Treatment with polysaccharides results in a reduction in IL8 secretion from keratinocytes; (b) Example data for the effects of *P. capsulatus* polysaccharide derivatives on IL8 gene expression by primary human keratinocytes after stimulation with 10 ng/ml of TNFalpha (all samples at 0.1 mg/ml). The data illustrates the % relative gene expression±SD, using TNFalpha only control as the calibrator, and GAPDH as a housekeeping gene. Fucoidan treatment run for comparison. Treatment with polysaccharide derivatives results in a reduction in IL8 gene expression by keratinocytes.

FIG. 10 illustrates the effects of *P. capsulatus* polysaccharide derivatives on IL8 release from primary human keratinocytes wherein there is provided example data for the effects of *P. capsulatus* polysaccharide derivatives (2-10 kDa) on IL8 release from primary human keratinocytes after stimulation with 10 ng/ml of TNFalpha, 20 ng/ml IL17A, or both in combination. The data illustrates the keratinocyte IL8 release in pg/ml for control wells (no stimulation or cytokine only) and wells treated with small polysaccharide derivatives, fucoidan, or NF-κB inhibitor SC-514. Treatment with polysaccharide derivatives results in a reduction in IL8 secretion from keratinocytes.

FIGS. 11*a* and 11*b* illustrate the dose-dependent effects of *P. capsulatus* polysaccharide derivatives on IL8, IL17C and IL6 release by primary human keratinocytes wherein (a) there is provided example data for the effects of *P. capsulatus* polysaccharide derivatives (2-10 kDa) on IL8 release from keratinocytes stimulated with 10 ng/ml TNFa & 50 ng/ml IL17A. The data indicates that the polysaccharide inhibits the release of IL8 in a dose-dependent fashion. It has greater potency at similar doses than the NF-κB inhibitor (SC-514), and the MAPK p38 inhibitor (SB203580). Low molecular weight (LMW) heparin is shown for comparison; (b) example data for the effects of *P. capsulatus* polysaccharide derivatives (2-10 kDa) on IL17C & IL6 release from keratinocytes stimulated with 10 ng/ml TNFa & 50 ng/ml IL17A & 10 microM histamine. The data indicates that the polysaccharide inhibits the release of IL17C & IL6 in a dose-dependent fashion. Low molecular weight (LMW) heparin is shown for comparison.

FIG. 12 illustrates the dose-dependent effects of *P. capsulatus* polysaccharide derivatives on IFNgamma release by primary human peripheral blood mononuclear cells wherein there is provided example data for the effects of *P. capsulatus* polysaccharides derivatives (2-10 kDa) on release of interferon gamma (IFNgamma) from peripheral blood mononuclear cells stimulated with 10 microg/ml phytohaemagglutinin and 10 ng/ml IL1beta. Data indicates that polysaccharide inhibits IFNgamma release in a dose-dependent fashion. This effect varies depending on the length of blood cell culture. Low molecular weight (LMW) heparin is shown for comparison.

FIG. 13 illustrates the effects of *P. capsulatus* polysaccharide derivatives on primary human neutrophil chemotaxis wherein there is provided example data for the effects of *P. capsulatus* polysaccharide derivatives on IL8 stimulated neutrophil chemotaxis (all samples at 0.1 mg/ml). Relative luminescent units±SD indicates the number of migrated neutrophils (which are visualised by a luminescent signal) in each treatment, where IL8 only is the control. Treatment with polysaccharide derivatives results in a reduction in neutrophil chemotaxis.

FIG. 14 illustrates the dose-dependent effects of *P. capsulatus* polysaccharide derivatives on THP-1 (monocyte) chemotaxis wherein this is provided example data for the effects of *P. capsulatus* polysaccharide derivatives (2-10 kDa) on MCP-1 (monocyte chemoattractant protein) stimulated THP-1 (pro monocytic cell line) chemotaxis. Treatment with polysaccharide results in a dose-dependent reduction of THP-1 chemotaxis. There is some variation between preparations, with the larger fragments showing greater inhibition (60-70%) although this could be a non-specific effect.

FIG. 15 illustrates the dose-dependent effect of *P. capsulatus* polysaccharide derivatives on mouse skin inflammation wherein there is provided example data for the effects of *P. capsulatus* polysaccharide derivatives (2-10 kDa) on imiquimod (IMQ) induced mouse skin inflammation after 9 days of IMQ treatment and polysaccharide dosing. Inflammation is measured by scoring of histological parameters including epidermal and keratinocyte proliferation, and leukocyte infiltration. The polysaccharide shows inhibition of skin inflammation in a dose-dependent manner.

* denotes statistical significance by ANOVA with Dunnett's post hoc analysis.

FIG. 16*a* illustrates a summary table of characterising features of *P. capsulatus* polysaccharide and polysaccharide derivatives thereof of the invention.

FIG. 16*b* illustrates the calculated sulphate content of *P. capsulatus* polysaccharides based on two different methods of analysis: a biochemical plate assay for sulphate (Terho method), compared with ICP-OES for sulphur (followed by a mathematical conversion to sulphate). The % sulphate detected is in good agreement between the two methods, confirming the high sulphate content of the polysaccharide.

EXAMPLES

Example 1

Growth of *Prasinococcus capsulatus* Strain Cultures

*P. capsulatus* strain cultures were maintained in the laboratory at 50 or 100 mL f/2 medium, with continuous light and at ambient (lab) temperatures (range throughout the year 18-28° C.). To set up the larger laboratory cultures, the stock culture was initially inoculated into 250 ml or 500 ml of f/2 medium and grown to log phase. 250 ml or 500 ml cultures were inoculated into 10 or 20 liter clear polycarbonate carboys with a vent screw with PTFE air inlet and air exhaust filters, containing f/2 medium autoclaved 116° C. for 30 mins. Inorganic phosphate and trace metals were autoclaved singly and separately added to the bulk of the medium after autoclaving.

Different amounts of $CO_2$/air mixes can be used, with different levels of illumination and temperature. Specifically 10 and 20 L cultures were sparged vigorously with air, with continuous illumination, using white fluorescent tubes at ambient (lab) temperatures: 18-28° C. deg range throughout year.

Alternatively many different pilot and large-scale culture systems could be used to grow *P. capsulatus*. Specifically a 200 liter pilot scale microalgal photobioreactor system (International patent WO2011/031161 A1; Norwegian patent 320950) was used with f/2 growth medium, aeration with air and 1-2% $CO_2$, and with continuous illumination (350 micromol/$m^2$/sec; 7-10 cm light path) between 18-28° C. temperature range.

Example 2

Harvesting Polysaccharide from Culture Medium

Polysaccharide can be obtained from culture medium by various centrifugation and filtration techniques. Specifically dense laboratory cultures (10-20 liters) were harvested and transferred to 4×600 ml centrifugation pots of Heraeus Multifuge 3L-R centrifuge. Centrifugation was at 4500 g for 2 hours per batch. The culture medium (supernatant) was transferred whilst the algal cells were pelleted in the centrifugation pot. The supernatant was further clarified by vacuum filtration (to remove residual cells), using a Whatman no. 3 filter.

This supernatant was then subjected to cross flow filtration using a Pall Centramate with a 0.1 $m^2$ SkDa molecular weight cut off (MWCO) T-series membrane. Other MWCO's can be used, as long as below MW of polysaccharide. Sample was refiltered through a Whatman No. 3 filter post-thawing, before being circulated through the membrane. Retentate was re-circulated until concentrated to ×10 original volume. This was then rediluted to original volume and repeated, to ensure salt and media components were removed in the permeate. Conductivity was monitored during the process. The retenate sample was collected and spray dried using a Buchi Mini Spray Dryer B-290 to provide dry polysaccharide powder. Further MWCO using any appropriate technique can be used to isolated target polysaccharide, but specifically separation using 300 kDa MWCO Vivaspin (Sartorius) by centrifugation was used to generate a high MW fraction.

Alternatively many different pilot and large-scale systems could be used to harvest polysaccharide from the culture medium of large-scale cultures. Specifically a disc stack Westphalia centrifuge was used to separate cultures from 200 liter photobioreactors running at 20-60 liters/hour. The culture was pumped directly into the disc-stack centrifuge from the microalgal photobioreactor, with the medium component being collected in an IBC.

The supernatant was then pre-filtered with a 5 micron filter (PURTREX PX05-9 7/8) and subjected to cross flow filtration using a Combi System M38-H-2.25-3 (Alfa Laval), with GR60P 25 kDa MWCO membranes. Sample was concentrated×10 and then 3 volumes of water (600 liters) were added to diafilter (removal of salts, medium components and low molecular weight material). Conductivity was monitored throughout, and the retentate sample collected. The polysaccharide containing retentate can be further spray dried using many different large-scale drying systems. Specifically a Mobile Minor spray drying system (GEA Process Engineering) was used, with inlet temperature of 200° C., and outlet temperature of 90-99° C., by atomising 2.3-2.7 kg/hour and recovering the dried polysaccharide from the cyclone and bag filter.

Example 3

Harvesting Polysaccharide from Cell Pellets

The cell pellets resulting from the removal of media can also be processed to generate target polysaccharide. This could be carried out by hot water extraction techniques, enzymatic digest or various other extraction protocols. Specifically cells were transferred to 50 mL sterile tubes and centrifuged for 2 h at 10,000 g. Remaining supernatant was removed and cells stored frozen for later extraction and processing. To process, the cells can be lysed and product removed using standard extraction techniques. Specifically cells were freeze-thawed three times prior to extraction. They were then mixed with an equal volume of Tris-HCl pH8, mixed with the enzyme alcalase 2.5 L DX (Novozyme) at a concentration of 1 vol enzyme to 100 vols sample, and incubated overnight at 60° C. with stirring. The sample was removed, spun at 10,000 g to pellet cell debris and the supernatant removed. This supernatant was dialysed against water using 8 kDa MWCO membrane using 10 volume batches of water with 4 changes over 36 hours. The desalted supernatant can be freeze or spray dried to generate a polysaccharide sample. Further MWCO using any appropriate technique can be used to isolated target polysaccharide, but specifically separation using 300 kDa MWCO Vivaspin (Sartorius) by centrifugation was used to generate a high MW fraction.

Example 4

Depolymerisation and Oligosaccharide Purification

High molecular weight target polysaccharide can be depolymerised into smaller fragments using techniques such as enzymatic digestion or acid hydrolysis. Specifically it can be depolymerised by introduction of hydrogen peroxide into a hot polysaccharide solution, to generate free radicals, which attack glycosidic bonds (Rota C et al. 2005 Free radical generation during chemical depolymerization of heparin. Anal Biochem. 344(2): 193-203. and Petit A C et al. 2006 Free-radical depolymerization with metallic catalysts of an exopolysaccharide produced by a bacterium isolated from a deep-sea hydrothermal vent polychaete annelid. Carbohydrate Polymers 64: 597-602.). Key variables are the ratio of hydrogen peroxide to polysaccharide, temperature and pH control. Solid polysaccharide sample was added to water at approximately 2 mg/ml, dissolved and warmed to 60° C. in a water bath with stirring. Copper salt solution was added to give a 0.01M concentration. Using a pH controller connected to a pump containing sodium hydroxide, the sample was set to pH 7.5. At this point the reaction is started by pumping hydrogen peroxide into the vessel at a constant flow rate, e.g. 0.5 ml/min, with the pH controller set to maintain the pH at 7 by turning the sodium hydroxide pump on when required. Once the reaction had been run for the desired period the pumps were stopped and pH was lowered using 20% acetic acid (5 microL/ml of reaction), chelex 100 (Sigma) was added at 60 mg/ml of reaction and the reaction is mixed on a rotating stirrer until clear. The whole reaction was removed from the chelex and stored at −20° C. Products were purified from the reaction by exchange of any remaining copper ions with sodium ions using Q-sepharose (GE)

anion exchange followed by desalting/separating by size exclusion chromatography by Superdex 30 (GE) using bench columns and Buchi Sepacore system with detectors for A214, A280 and conductivity. The Q-sepharose column was equilibrated in 50 mM Tris-HCl pH7.5, 50 mM sodium chloride mobile phase, followed by loading of the depolymerisation reaction, and washing for a further 20-30 mins with mobile phase all at 10 ml/min. Then the bound polysaccharide was eluted with 5M sodium chloride solution and collected. The eluate was added in 5 ml batches to a size exclusion bench column Superdex30 at 1 ml/min with water as mobile phase. Separation was carried out over 120 mins, with 3 ml fractions collected using a Pharmacia fraction collector. Fractions of different polysaccharide molecular weight ranges were identified, pooled, and freeze-dried. Specifically two size ranges were normally collected representing 2-10 kDa and 20-60 kDa derivatives but other sizes may be collected. Stock solutions of derivatives were injected onto a size exclusion HPLC column (Biosep4000, YMC Diol300 or YMC Diol120) to confirm approximate molecular weight (see below).

Example 5

Determination of Approximate Molecular Weight

Polysaccharide and polysaccharide derivative molecular weight was estimated by size exclusion chromatography using a Waters Alliance HPLC (2695) with Refractive index (Waters 2410) and Photodiode Array (210-380 nm) detection (Waters 996). Either YMC300-Diol or Biosep4000 size exclusion columns were equilibrated at 30-37° C. in 0.2 micron filtered 50 mM Tris-HCl pH7, 1 mM EDTA, and 0.9% NaCl mobile phase. Columns were calibrated using dextran standards (Fluka: 12, 27, 50, 80, 270, 670 kDa), by injecting 20 microL in mobile phase, running at 0.5 or 1 ml/min (YMC300 or Biosep4000) with 10 or 15 minute isocratic separations. The standard curve was generated using the formula Kay=(retention time–V0)/(Vt–V0), and plotting Kay versus molecular weight. Samples were injected at 20 microL of a 0.1 mg/ml solution in mobile phase and run as per standards. Data was manually integrated with Millennium Waters software, with or without blank baseline subtraction. The retention times of the sample were compared to those generated for the standard curve to calculate approximate molecular weight using the formula above.

Further, the molecular weight of the native *P. capsulatus* polysaccharide can be estimated by sedimentation equilibrium techniques. Specifically sedimentation equilibrium using a Beckman XL-I analytical centrifuge (AUC) equipped with scanning absorption optics was used. Samples were resuspended at 0.5 mg/ml in 0.1M sodium chloride in water. A sedimentation velocity experiment was carried out to assess sample confirmation and heterogeneity, and assess required parameters for subsequent sedimentation equilibrium. Sedimentation equilibrium was carried out at rotor speed of 1400 rpm and 1 mm column.

Example 6

Determination of Approximate Sulphate Content

Various methods may be used to determine sulphate content of target polysaccharide and polysaccharide derivatives. Specifically sulphate determination was carried out based on a method by Terho T & Hartiala K (Method for the determination of sulphate content of glycosaminoglycans. Analytical Biochemistry (1971) 41 (2): 471-476). 25 µl of 1 mg/ml sample or control (chondroitin Sigma C4384 or heparin Sigma H3393) in water was placed in a reaction vial. 1M HCl was added to give a final concentration of 0.5-1M HCl and the vials heated at 100° C. for 2 hours. The hydrolysed sample was rotary evaporated using a Speed Vac (Jouan RC10/10 with RCT60 refrigerated trap) under vacuum at 60-65° C. until dry (usually 1-2 hours). The dried hydrolysate was dissolved in 250 microL of water (0.1 mg/ml).

Standards were prepared from 1 mM sulphuric acid to give concentrations in the assay of 0.048, 0.096, 0.192, 0.288, 0.384, 0.432, 0.48 µg sulphate. 100 microL of each sample, standard, control or blank (water only) were pipetted into an eppendorf, to which 400 microL of ethanol was added and mixed thoroughly. 125 microL of this mix was added to triplicate wells of a 96 well assay plate, 50 µl $BaCl_2$ buffer (freshly prepared 0.2M Acetic acid, 0.1 mM barium chloride, 1.6 mM sodium hydrogen carbonate all in absolute ethanol) was added to each well, followed by 75 µl sodium rhodizonate solution (freshly prepared 0.05 mg/ml, 1 mg/ml L-ascorbic acid in absolute ethanol). The plate was shaken at medium speed for 30 secs, incubated in the dark for 10 minutes and shaken again. Colour intensity was measured in an absorbance microplate reader (BioTek Power Wave HT) at 520 nm using GenS software. Absorbance was calculated by subtracting the mean absorbance for each sample, standard or control from the mean absorbance of the blank. A standard curve was generated by plotting the blanked absorbance against the sulphate concentration for each sulphuric acid standard, and the sulphate content of samples and controls was interpolated. This value is corrected for dilutions and volumes to give % sulphate= ((Mean$\Delta$A520×40)/50)×100.

Sulphate determination was also carried out by inductively coupled plasma optical emission spectrometry (ICP-OES). 10 mg of polysaccharide was resuspended in 1 ml water and then extracted in nitric acid: hydrochloric acid (aqua regia). Samples were nebulised and the aerosol produced was transported to a plasma torch where excitation occurred. Characteristic atomic line spectra for sulphur were produced by a radio-frequency inductively coupled plasma. The spectra were dispersed by a grating spectrophotometer and intensities of the lines were monitored by photomultiplier tubes. The photocurrents from the photomultiplier tubes were processed and sulphur content calculated based on sulphur standards (multipoint calibration) and converted to sulphate value by mathematical formula.

Example 7

Determination of Monosaccharide Composition

Monosaccharide composition can be determined using a number of different methods. Specifically, monosaccharide composition was determined by methanolysis and trimethylsilane (TMS) derivatisation followed by composition analysis using Shimadzu GC-2014 with flame ionisation detection (GC-FID). Reaction vials were heat cleaned in a furnace oven for 6 hours at 450° C. 100 microg of sample (as a 10 mg/ml solution) was transferred to a vial and 5 nmol of scyllo-inositol internal standard was added to each sample. A vial containing 5 nmol of each monosaccharide standard was also set up containing scyllo-inositol (18132 Sigma), arabinose (A3131 Sigma) xylose (X-1500 Sigma), mannose (M6020 Sigma), fucose (F2252 Sigma), rhamnose (R3875 Sigma), galactose (G0750 Sigma), glucose, glucosamine (G4875), galactosamine (G0500), glucuronic acid (G5269), galacturonic (48280 Fluka), sialic acid (all prepared as 100 mM stock solutions). All vials were dried in a speed-vac (Jouan RC10/10 with RCT60 refrigerated trap) under vacuum at 60-65° C. until dry (usually 1-2 hours). 40 microL of neat methanol was added, the samples dried again as above and then resuspended in 100 microL of 0.5M methanolic HCl. The vials were heated at 85° C. in a heat bloc for 4 hours. After cooling 20 microL neat pyridine was added to neutralise the HCl and 20 microL neat acetic anhydride was then added to re-N-acetylate any free primary amines (for 30 minutes at room temperature). The vials were then dried again (speed vac as above), 40 microL of neat methanol was added to wash, the vials were re-dried (10-30 mins speed vac as above). 40 microL of neat TMS reagent was then added and mixed thoroughly to resuspend the sample. The vials were sealed and left for at least 10 minutes before injecting 1 microL onto a Shimadzu GC-2014 with flame ionisation detection (300° C. splitless injection). The column was ZB5-ms, 30 m×0.25 mm i.d.×0.25 μm film thickness. The chromatograms generated were analysed. The area cut off was manually adjusted for each sample until 20-30 peaks were identified. Peak areas and retention times were correlated with the monosaccharide standards.

Each peak was calculated:
ratio=peak area/internal standard peak area;
standard ratio=standard area/internal standard area for each standard;
nmoles=(5 nmoles/standard ratio)×sample ratio;
% of each monosaccharide present in the original sample=nmoles/total nmoles×100.

Monosaccharide composition of *P. capsulatus* polysaccharide was also determined by trifluoroacetic acid (TFA) hydrolysis followed by high performance anion exchange chromatography with pulsed amperometric detection (HPAEC-PAD).

Samples of *P. capsulatus* polysaccharide and derivatives were resuspended at approximately 10 mg/ml in 2M TFA. They were incubated at 120° C. for 1 hour in a heating block, with vigorous shaking after 30 mins. They were then centrifuged and the supernatant recovered. The pellet was washed with 0.5 ml of water, re-centrifuged and the wash pooled with the original supernatant. The recovered solution was dried in vacuo to remove the TFA and the dry residue was resuspended in 1 ml of water. A 1/10th dilution of the sample was injected onto a Dionex PA1 column along with a dilution series of standard monosaccharides, disaccharides and uronic acids. (This mix contained fucose, rhamnose, arabinose, galactose, glucose, xylose, mannose, ribose, cellobiose, maltose, galacturonic acid, glucuronic acid.). Samples were separated by gradient and resolved with PAD. Recovery of monosaccharides was calculated by comparison to standards.

10 microL of the TFA hydrolysates (nominally 100-160 microg of polysaccharide) were also loaded onto 2 sheets of Whatman number 20 paper. Monosaccharide standards mix—ribose, rhamnose, xylose, fucose, arabinose, mannose, glucose, galactose, galacturonic acid—was also loaded. Paper chromatography was carried out by running one sheet in butanol/acetic acid/water 12:3:5 mobile phase for 30 hours, and the other in ethyl acetate/pyridine/water 8:2:1 mobile phase for 3 days with separation by charge. Sheets were stained with aniline hydrogen-phthalate to visualise monosaccharides.

Example 8

Determination of Cytotoxicity

Various different cell-based screening assays can be used to determine the cytotoxicity of the target material. Specifically cytotoxicity is examined by measuring the effects of the polysaccharide and polysaccharide derivatives on the metabolic activity of a BHK cell line (hamster kidney fibroblast ECACC 85011433). 90% confluent BHK cells are harvested and plated in a 96-well white microplate at $1 \times 10^4$ cell/well in 100 microL freshly prepared culture media (Glasgow Minimum Essential Medium (GMEM), 10% Foetal Calf Serum, 5% Tryptose Phosphate Broth, 2 mM L-Glutamine). They are left for 1 hour at 37° C. 5% $CO_2$ to allow>80% adhesion to the well. 11 microL of 1 mg/ml polysaccharide sample in Hanks Balanced Salt Solution (HBSS), HBSS only control, fucoidan (1 mg/ml in HBSS) control, and doxorubicin (10 microg/ml, 1 microg/ml in HBSS) controls are added to triplicate wells and the plate incubated for 16-18 hours at 37° C. 5% $CO_2$. The plate is allowed to come to room temperature for 30 minutes before additions of 100 microL Cell titre glow reagent (Promega). Plate is mixed for 2 minutes on a plate shaker and then incubated for 10 minutes at room temperature. The resulting luminescence for each well is measured on plate reader (BioTek, Synergy 3) using GenS software. Mean luminescence for each sample or control is calculated. The HBSS control well is designated as 100% metabolic activity and sample luminescent values are calculated against this % activity=(test well/control well)*100. The fucoidan and doxorubicin controls should be within established values.

Example 9

Effects on Neutrophil Elastase Activity

Different protocols are possible for the measurement of the effect of polysaccharide on neutrophil elastase enzyme activity. Specifically elastase activity was measured by incubation of polysaccharide with stimulated freshly isolated human neutrophils followed by reaction of released enzyme with a labelled substrate and colourimetric measurement on a plate reader. Freshly isolated human neutrophils were resuspended in HBSS (without Ca and Mg) and cells counted on a haemocytometer. The cells were centrifuged and resuspended in HBSS to give a concentration of $2.5 \times 10^6$ cells/ml. 22 microL of sample, controls or HBSS were added to a microtube followed by: 25 microL of cytochalasin B (at 40 mg/ml in HBSS to give a final concentration 5 mg/ml); 25 microL of TNF a (at 80 ng/ml in HBSS to give a final concentration of 10 ng/ml, with 25 microL HBSS used in place of TNF a for a non-stimulated control); 150 microL of neutrophil suspension (or for a media only control group add 150 microL of HBSS in place of cells). Contents were gently mixed and the tubes incubated at 37° C. for 30 minutes. After incubation 25 microL of fMLP (at 1 microg/ml in HBSS to give a final concentration of 100 ng/ml) was added, or HBSS to the non-stimulated control group. Tubes were incubated for a further 45 minutes at 37° C. Tubes were centrifuged at 5000 rpm for 5 minutes on a Heraeus Biofuge to pellet the cells and 25 microL of the supernatant is transferred into triplicate wells of a 96 well black microplate. 150 microL of Tris HCl pH 7.5 and 20 microL of neutrophil elastase substrate 1 (0.5 mg/ml in Tris-HCl pH 7.5) were added to each well, except for a blank well which contains no substrate. The plate was transferred to a prewarmed (37° C.) plate reader (BioTek Powerwave HT) and readings are taken at 405 nm every 5 minutes for 1 hour using GenS software. Vmax was calculated over 4 data points between 10 minutes and 1 hour. Mean Vmax was calculated for each sample, control or blank. The control well (stimulated cells with substrate, but no test samples) Vmax was designated as 100% and samples and controls are calculated against this to generate % elastase activity: % activity=(test well Vmax/control well Vmax)*100.

Example 10

Effects on Keratinocyte Cytokine Release and Gene Expression

The effects of polysaccharides and polysaccharide derivatives on keratinocyte cells may be assessed using a range of different cell lines or primary cells, in various different growth media with or without pro-inflammatory stimulus. The resulting cytokine release can be assessed by different methods such as multiplex arrays or ELISA's. Specifically primary keratinocytes (Promocell C12003) were grown in full keratinocyte growth media with calcium and supplements (Promocell C20011) at 37° C., 5% $CO_2$ until 70-90% confluent. They were harvested by trypsinisation, washed and seeded in the wells of a 24 well plate tissue culture plate at 30,000 cells per well. Cells were grown until ~80-90% confluent (~56 hours) and the media was then changed to basal media (Promocell C20211) with 0.5 mM calcium, for a further 16-18 hours. Samples (1 mg/ml in HBSS), controls (fucoidan 1 mg/ml in HBSS) or blanks (HBSS vehicle only) were then added to the wells (×10 dilution) for 6-8 hours before addition of pro-inflammatory stimulus, or 1-2 hours in the case of SC514 and SB203580 (NfkB and MAPK p38 inhibitor respectively). Pro-inflammatory stimulus was either 10 ng/ml TNFalpha or 10 ng/ml IL1beta or 20 ng/ml IL17A, or both 10 ng/mlTNFalpha and 20 ng/mlIL17 in combination. Other stimuli were 10 ng/ml TNFalpha and 50 mg/mlIL17A in combination, or 10 ng/ml TNFalpha, 50 mg/mlIL17A and 10 microM histamine in combination. Cells were incubated for a further 16-18 hours at which point the supernatant was collected and stored at −80° C. During collection the supernatant was replaced with PBS to wash the cells and then this was replaced with 350 microL RNAeasy lysis buffer (Qiagen). Buffer, lysed cells and cell content were transferred to tubes for storage at −80° C.

The collected supernatant was analysed for human IL8, IL6 or IL17C content by ELISA (Peprotech for IL8 and IL6; R and D Systems for IL17C). The assay was read on a microplate reader (BioTek PowerWave HT using GenS software) at A450-630 nm, and quantification was made by reading off the standard curve. The concentration of cytokine in the unstimulated control was subtracted from the concentrations in the test wells and stimulated control well. The stimulated control well was designated as 100% secretion of IL8 and samples were calculated against this % secretion=(corrected test well pg/ml/corrected control well pg/ml)*100.

RNA was extracted from the cell lysate using a Qiagen RNAeasy Plus Kit. The resulting RNA was quantified on a spectrophotometer to check concentration range. cDNA was generated by using Qiagen Quantitect Reverse Transcription kit (starting volume of RNA is 4 microL) with genomic DNA removal by enzymatic digestion, prior to the RT step. cDNA was add to a PCR reaction (1 or 2 microL) containing primers for either IL8 (Qiagen) or GAPDH (Qiagen) as the housekeeping gene, and Qiagen QuantiFast SYBR PCR master mix (25 microL reaction volume). PCR was carried out on an Mx3005P Real-time PCR machine (Stratagene) using standard settings (60° C. annealing and extension, 40 cycles). Cycle threshold (Ct) values were obtained for test and control samples using MxPro software. Relative expression of target genes was assessed by comparison of target gene and housekeeping gene (comparative expression by $\Delta\Delta CT$ method, with target and housekeeping gene PCR showing comparable amplification efficiencies), and with the stimulated control well cDNA designated as the calibrator sample (100% gene expression).

Example 11

Effects on Cytokine Release from Stimulated Human Peripheral Blood Mononuclear Cells (PBMC's)

The effects of substances on the release of cytokines from PBMC's can be measured using many different cell formats, stimuli and durations. Specifically the effects of P. capsulatus polysaccharide derivatives were measured by incubation with isolated PBMC's. PBMC's were isolated from fresh blood by histopaque (Sigma) gradient centrifugation, washed in modified HBSS medium (PAA), and resuspended in complete RPMI 1640 medium (PAA). 200,000 PBMC's were added to a 96 v-well polypropylene plate, along with media only controls. Polysaccharides at selected concentrations, along with controls SC514 and SB203580 (NfkB and MAPK p38 inhibitor respectively) were added to cells and incubated for 1 hour at 37° C., 5% $CO_2$. Phytohaemagglutinin (PHA) (10 microg/ml) and IL1beta (10 ng/ml) were added to each well except for unstimulated controls and plates were incubated at 37° C., 5% $CO_2$ for 2 or 3 days. To collect media, plates were centrifuged at 1000 rpm and the supernatant transferred to a further plate for storage at −80° C., prior to cytokine analysis. The collected supernatant was analysed for interferon gamma (IFNgamma) content by ELISA (Peprotech). The assay was read on a microplate reader (BioTek PowerWave HT using GenS software) at 450-630 nm and quantification was carried out by reading off the standard curve. The concentration of cytokine in the unstimulated control was subtracted from the concentrations in the test wells and stimulated control well. The stimulated control well was designated as 100% secretion of IFNgamma and samples were calculated against this control=(corrected test well pg/ml/corrected control well pg/ml)*100

Example 12

Effects on Oxidative Burst from Neutrophils

There are numerous protocols to measure the production of reactive oxygen species from immune cells, using different cells, stimuli and substrates. Specifically inhibition of the oxidative burst by polysaccharide and polysaccharide derivatives was measured using human neutrophils, which were stained with the reagent DCFH-DA. Freshly isolated human neutrophils were resuspended in HBSS (without Ca and Mg) and cells counted on a haemocytometer. Cells were resuspended at $1 \times 10^6$ in HBSS, mixed with an equal volume of DCFH-DA at 40 microM in HBSS and incubated for 30 mins at 37° C., 5% $CO_2$. 100 microL of stained cells were added to each well of a black 96 well microplate, apart from triplicate wells of a blank (HBSS only) and unstained cells control. 20 microL of 1 mg/ml of samples, HBSS or controls (diphenyleneiodium chloride (DPI) 1 microM concentration in HBSS) were added to triplicate wells containing stained cells. Cells were stimulated to produce ROS by the addition of 50 microL of PMA (4 nM in HBSS), except for no stimulation control wells. Fluorescence generated by the oxidation of DCFH-DA by ROS was measured on a fluorescent plate reader (Biotek Synergy 3) at 37° C., 485/528 nm kinetic read every 10 minutes for 2.5 hours. Mean fluorescence is calculated, and blanked. Mean fluorescent data for the PMA stimulated cells was designated as 100% response and samples and controls were evaluated against this: % oxidative burst=(sample fluorescence/PMA stimulated cells fluorescence)*100.

Example 13

Effects on Blood Cell Chemotaxis

A chemotaxis assay can be carried out using different types of immune cell, with different chemotactic agents. Specifically the effects of polysaccharide and polysaccharide derivatives on the chemotaxis of neutrophils were measured. Human neutrophils are isolated from fresh blood using Histopaque. 90 microL of freshly isolated neutrophils at $2.5 \times 10^6$/ml in HBSS including BSA 0.1%, 25 mM HEPES (Sigma), are mixed with 10 microL of test compound (at selected concentration eg. 2-50 microM) or vehicle controls, in each well of a polypropylene 96 well plate (Greiner) and pre-incubated for 30 minutes. While cells and test compounds are pre-incubating the lower chamber of a chemotaxis 96 well plate (3 micron mesh) (Corning) is prepared. IL8 (Sigma) is made up in HBSS including BSA 0.1%, 25 mM HEPES, at required dose (eg. 0.37 ng/ml to 10 ng/ml final concentration). 235 microL is added per lower assay chamber. For negative controls 235 microL of HBSS (with Ca/Mg, BSA 0.1%, 25 mM HEPES) is used in place of IL8. The lower assay chamber is then incubated at 37° C. CO2 5% for 30-60 mins to pre-equilibrate media. The upper wells are then carefully transferred to the lower and 75 microL of neutrophils from each well of the polypropylene pre-incubation plate is added to a well in the upper chamber of the chemotaxis plate. The whole plate is incubated at 37° C. CO2 5% for 30 min.

The assay plate is removed from the incubator. The upper well contents are discarded and the upper wells are transferred to a white 96-well plate containing Accutase enzyme (Sigma) at 180 microL per well at room temperature. The plate is placed on a plate shaker for 5 mins at room temperature. The upper chamber is discarded and the number of cells present in the white plate is measured using Cell Titer Glow reagent (Promega) according to the manufacturers instructions (see also example 8). 100 microL CellTiter-Glo reagent is added per well of the 96-well luminescence plate containing the mesh cells and Accutase and mixed on a plate shaker for 2 min RT then incubated for 10 min RT. The luminescence signal is measured on a Synergy 2 plate reader using Gen 5 software. Data is blanked against the media plus cells only control and the % migration calculated by comparison to the IL8 only chemotaxis 100% control.

Further, effects of P. capsulatus polysaccharide derivatives on the chemotaxis of monocytes, using THP-1 human pro-monocytic cell line (HPA 88081201) were also assessed. Polysaccharide derivatives (triplicate wells) at selected concentrations were mixed with THP-1 cells at $2 \times 10^6$/ml in RPMI 1640 medium (PAA) with 25 mM HEPES, 2 mM Glutamine and 0.1% BSA (Sigma) in a 96 v-well polypropylene (PP) plate (Greiner). A cells only control was also set up in triplicate. The cells and polysaccharides were incubated at 37° C. 5% CO2 for 30 minutes. 235 microL of 10 ng/ml of monocyte chemoattractant protein-1 (MCP-1) (Peprotech) in the same medium was added to the lower chamber of a 96 well 5 micron mesh chemotaxis plate (Corning), using assay medium as a negative control. The upper plate was refitted and the plate incubated at 37° C. 5% CO2 for 30 minutes to pre-equilibrate media. The assay was carried out by transferring 75 microL of THP-1 cells (~150, 000 cells) and test samples from the PP plate into the upper chamber of the MCP-1 containing chemotaxis plate. Care was taken to ensure cells were fully suspended and mixed well before transfer. The plate was incubated at 37° C. 5% CO2 for 120 minutes. Chemotaxis was measured by removing media from the upper chamber, transferring the membranes to a plate containing 180 microL of Accutase enzyme (Sigma), shaking for 5 minutes and discarding membranes. 100 microL CellTiter-Glo reagent (Promega—as for neutrophil chemotaxis) was added to the lower well of the assay plate and to the Accutase containing plate. They were shaken for 2 minutes, incubated for 10 minutes and then 200 microL of the well contents was transferred to a white 96-well plate and the luminescence measured on a Synergy 2 plate reader (Biotek) using GenS software. Data was blanked using the media and cells only control, values were pooled from the lower chamber and accutase samples, and % chemotaxis was calculated by comparison to the cells only MCP-1 control wells (100% chemotaxis).

Example 14

Effects on Skin Inflammation in Imiquimod (IMQ) Treated BALB/c Mice

There are numerous protocols to assess the effects of test substances on skin inflammation in mouse models, using different types of mice, genetic inducers and external stimuli. Specifically the effects of P. capsulatus polysaccharide derivatives on skin inflammation were assessed using an IMQ-induced BALB/c mouse model. Test groups included a naïve plus vehicle group, an IMQ only group, an IMQ plus vehicle group, a polysaccharide plus vehicle group at 3 different concentrations (1, 0.1, 0.01%) and a cyclophosphamide control (10 mg/kg in 0.5% CMC), with 8 mice per group. Polysaccharides were dissolved in an aqueous gel containing a polyacrylate sodium salt, glycerol, paraben and imidazolidinyl urea (=vehicle). 500 microL of test gels were applied daily to the shaved backs of mice, 4 hours prior to the application of 50 mg of IMQ cream (5%). Vaseline was used in the case of naïve mice test group and the cyclophosphamide was dosed orally once a day. Observations of skin appearance (scaling, folding, erythema) were made each day to provide a disease activity index. Dosing was repeated for 4 days, after which 4 mice from each group were sampled, and then until Day 9 of the experiment when all remaining mice were sampled. Skin samples from all mice were fixed in formalin, embedded, sectioned and stained with haematoxylin and eosin. Slides were scored for epithelia hyperplasia, keratinocyte proliferation (hyperkeratosis), leukocyte infiltration and increased vascularisation. Scores were plotted against test agents to determine the effects of polysaccharide treatment compared to IMQ plus vehicle controls.

Although the invention has been particularly shown and described with reference to particular examples, it will be understood by those skilled in the art that various changes in the form and details may be made therein without departing from the scope of the present invention.

The invention claimed is:

1. An oligosaccharide derivative of a gel forming polysaccharide, wherein the polysaccharide is obtainable from microalgal cells from the order *Prasinococcus capsulatus* wherein the gel forming polysaccharide is a sulfated heteropolymer of molecular weight of at least 670 kDa comprising glucose, galactose, arabinose and uronic acid units, wherein said derivative has a molecular weight in the range of about 2 kDa to 60 kDa.

2. A derivative as claimed in claim 1 wherein the derivative has a molecular weight in the range 2 to 10 kDa.

3. A derivative as claimed in claim 2 wherein the derivative comprises by weight about
   30 to 40% Glucose
   30 to 40% Galactose
   8 to 14% Arabinose
   7 to 11% Uronic acid
   and 1 to 10% of other sugar units.

4. A derivative as claimed in claim 1 wherein the derivative has a molecular weight in the range 20 to 60 kDa.

5. A derivative as claimed in claim 4 wherein the derivative comprises by weight about
   25 to 28% Glucose
   35 to 55% Galactose
   8 to 17% Arabinose
   4-6% Uronic acids
   and 1 to 5% of other sugar units.

6. A derivative as claimed in claim 1 wherein the derivative inhibits neutrophil elastase release by about 70 to 90%.

7. A derivative as claimed in claim 1 wherein the derivative inhibits neutrophil reactive oxygen species production by about 30-40% relative to neutrophils to which derivative has not been provided.

8. A derivative as claimed in claim 1 wherein the derivative inhibits human keratinocyte IL-8 gene expression and IL8 release by about 70 to 100% relative to keratinocyte to which derivative has not been provided.

9. A composition comprising a derivative, as claimed in claim 1.

10. A cosmetic preparation comprising a derivative as claimed in claim 1.

11. A nutritional supplement comprising a derivative as claimed in claim 1.

12. A method for prophylaxis or treatment of an immune system disorder comprising administering the derivative of claim 1 to an animal in need thereof.

13. The method of claim 12 wherein said immune system disorder is an inflammatory skin condition selected from the group consisting of eczema, psoriasis and atopic dermatitis.

14. The method of claim 12 wherein said immune system disorder is an inflammatory condition of the gut selected from the group consisting of irritable bowel syndrome, Crohn's disease and ulcerative colitis.

15. The method of claim 12 wherein said immune system disorder is an inflammatory condition of the respiratory system selected from the group consisting of asthma, cystic fibrosis, emphysema, chronic obstructive pulmonary disorder, acute respiratory distress syndrome, and allergic rhinitis.

* * * * *